(12) United States Patent
Kim et al.

(10) Patent No.: US 7,285,652 B2
(45) Date of Patent: Oct. 23, 2007

(54) ISOLATED NUCLEIC ACID MOLECULE ENCODING THE MODIFIED PHYTOCHROME A

(75) Inventors: Jeong-Il Kim, Kwangju (KR); Yun-Jeong Han, Kwangju (KR); Pill-Soon Song, Kwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 159 days.

(21) Appl. No.: 11/129,459

(22) Filed: May 16, 2005

(65) Prior Publication Data

US 2006/0260009 A1 Nov. 16, 2006

(51) Int. Cl.
C07H 21/04 (2006.01)
(52) U.S. Cl. .................................... 536/23.1
(58) Field of Classification Search ............... None
See application file for complete search history.

(56) References Cited

U.S. PATENT DOCUMENTS 6,916,973 B2 * 7/2005 Kim et al. ............ 800/298
2003/0204872 A1 * 10/2003 Kim et al. ............ 800/282

OTHER PUBLICATIONS

Hershey et al., Analysis of cloned cDNA and genomic sequences for phytochrome: complete amino acid sequences for two gene products expressed in etiolated Avena, Nucleic Acids Research, vol. 13 No. 23 1985 pp. 8543-8559.*
Reed et al., "Phytochrome A and Phytochrome B Have Overlapping but Distinct Functions in *Arabidopsis* Development", Plant Physiol. (1994) 104: 1139-1149.
Johnson et al., "Photoresposes of Light-Grown phyA Mutants of *Arabidopsis*", Plant Physiol. (1994) 105:141-149.
Heyer et al., "Function of Phytochrome A in Potato Plants as Revealed through the Study of Transgenic Plants", Plant Physiol. (1995) 109: 53-61.
Botto et al., "Phytochorme A Mediates the Promotion of Seed Germination by Very Low Fluences of Light and Canopy Shade Light in *Arabidopsis*", Plant Physiol. (1996) 110: 439-444.
Morelli et al, "Shade Avoidance Responses. Driving Auxin along Lateral Routes", Plant Physiology, Mar. 2000, vol. 122 pp. 621-626.
Boccalandro et al., "Increased Phytochrome B Alleviates Density Effects on Tuber Yield of Field Potato Crops", Plant Physiology, Dec. 2003, vol. 133, pp. 1539-1546.
Devlin et al., "A Genomic Analysis of the Shade Avoidance Response in *Arabidopsis*", Plant Physiology, Dec. 2003, vol. 133, pp. 1617-1629.
Boylan et al., "Oat Phytochrome Is Biologically Active in Transgenic Tomatoes", The Plant Cell, vol. 1, pp. 765-773, Aug. 1989.
Kim et al., "Phytochrome Phosporylation Modulates Light Signaling by Influencing the Protein-Protein Interaction", The Plant Cell, vol. 16, pp. 2629-2640, Oct. 2004.

Smith et al., "The shade avoidance syndrome: multiple responses mediated by multiple phytochromes", Plant, Cell and Environment (1997) 20, 840-844.
Shlumukov et al., "Establishment of far-red high irradiance responses in wheat through transgenic expression of an oat phytochrome A gene", Plant, Cell and Environment (2001) 24:703-712.
Sineshchekov et al., "Fluorescence and photochemical properties of phytochromes in wild-type wheat and transgenic line overexpressing an oat phytochrome A (PHYA) gene: functional implications", Plant, Cell and Environment (2001) 24:1289-1297.
Clough et al., "Floral dip: a simplified method for Agrobacterium-mediated transformation of *Arabidopsis thaliana*", The Plant Journal (1998) 16(6):735-743.
Sullivan et al., "From seed to seed: the role of photoreceptors in *Arabidopsis* development", Developmental Biology 260 (2003) 289-297.
Mockler et al., "Regulation of photoperiodic flowering by *Arabidopsis* photoreceptors", PNAS, Feb. 18, 2003, vol. 100, No. 4, 2140-2145.

(Continued)

*Primary Examiner*—Kenneth R. Horlick
*Assistant Examiner*—Mark Staples
(74) *Attorney, Agent, or Firm*—Kenyon & Kenyon LLP

(57) ABSTRACT

The present invention includes modified phytochrome A (PHYA) nucleic acid molecules in which Pr absorption spectra have been shifted to longer wavelength (i.e. bathochromism or red-shift). The plants with the bathochromic phytochromes are expected to respond to canopy and shade conditions for growth and development with greater efficiency than the plants with wild-type phytochrome (i.e. suppression of shade avoidance reactions in plants). Since the shade avoidance reactions in plants induce a rapid and dramatic increase in the extension growth of stems and petioles at the expense of leaf growth, storage organ production, and reproductive development, it causes significant losses of crop yields. Thus, the bathochromic phytochromes that utilize the shade light efficiently would suppress the shade avoidance reactions in plants, giving plants the tolerance to shade. In this invention, several bathochromic phytochromes were generated by site-directed mutagenesis in the region of bilin lyase domain in plant PHYA, and their ability to suppress the shade avoidance reactions were examined by transforming the bathochromic phytochromes into PHYA deficient *Arabidopsis thaliana* (ecotype col-0). The transgenic plants with the bathochromic phytochromes showed significantly increased shade tolerance compared to wild-type plants and transgenic plants with wild-type phytochromes. Therefore, the present invention can be utilized to suppress plants' shade avoidance that is one of major causes to induce crop-yield losses, and ultimately to generate shade tolerant plants with higher yields. The invention also includes plants having at least one cell expressing the modified PHYA, vectors comprising at least one portion of the modified PHYA nucleic acids, and methods using such vectors for producing plants with shade tolerance.

4 Claims, 7 Drawing Sheets

OTHER PUBLICATIONS

Cerdàn et al., "Regulation of flowering time by light quality", Nature, vol. 423, Jun. 19, 2003.

Kim et al., "Phytochrome-mediated signal transduction pathways in plants", Biochemical and Biophysical Research Communications 298 (2002) 457-463.

Hayama et al., "Shedding light on the circadian clock and the photoperiodic control of flowering", Current Opinion in Plant Biology 2003, 6:13-19.

* cited by examiner

| Overlapped areas of shade and phytochrome spectra | |
|---|---|
| PhyA | 100 % |
| Blue-8 (8 nm blue-shifted) | 67 ± 4 % |
| Red-8 (8 nm red-shifted) | 153 ± 4 % |
| Red-12 (12 nm red-shifted) | 176 ± 4 % |

(A)

(B)

(A)

(B)

ISOLATED NUCLEIC ACID MOLECULE ENCODING THE MODIFIED PHYTOCHROME A

SEQUENCE LISTING

The instant application contains a Sequence Listing which has been submitted via CD-R, and is hereby incorporated by reference in its entirety. Said CD-Rs, created on Aug. 9, 2005, are labeled "Copy 1 Replacement", "Copy 2 Replacement" and "CRF", respectively, each contains one identical 156 KB file identified as 1942.59 Sequence Listing.txt.

BACKGROUND OF THE INVENTION

1. Field of the Invention

This invention relates to a modified phytochrome A (PHYA) nucleic acid molecule of which Pr absorption spectra have been shifted to longer wavelength (i.e. bathochromic or red-shifted phytochrome A), in order to give plants shade-tolerance that increases crop yields. The phytochrome A functions as the photoreceptor in far-red wavelength light in mediating the suppression of shade avoidance and the development of plants. These bathochromic phytochromes absorb and utilize light even in the canopy and shade conditions, which suppresses shade avoidance reactions in plants (i.e. shade tolerance). Since the shade avoidance reactions re-distributes energy and resources to unnecessary elongation and acceleration of senescence (i.e. early flowering), it causes drastic reduction in products such as leaves, storage organs and seeds. Thus, the developed bathochromic phytochromes enable us to develop shade tolerant plants with high yields. The present invention also provides the methods and processes for generating transgenic plants transformed with the said nucleic acid molecules to engineer shade tolerance of economically important crop plants for high-yielding.

2. Description of Prior Art

Light is the most important environmental factor for optimal growth and development of plants (Chen et al., 2004). They harness not only energy from light for anabolic pathways that construct their building blocks, but also adapt to changes in light during their life cycle from germination to flowering. Phytochrome is a photoreceptor that manage a variety of photomorphogenic responses to the red/far-red region of the spectrum (Smith, 2000). They are dimeric chromopeptides (monomer sizes of 120~130 kDa) that carry the chromophore phytochromobilin (PΦB), which is covalently linked to a cysteine residue on each peptide via a thioether linkage. There are two spectrally distinct forms of phytochromes, a red-light (R, λmax=660 nm) absorbing Pr form and a far-red light (FR, λmax=730 nm) absorbing Pfr form (FIG. 1A). The latter form is considered as the active form of phytochrome because of the promotive effect of red-light on most physiological responses. Phytochrome signaling in plants is driven by phototransformation between the two forms (Kim et al., 2002).

Competition for sunlight is one of the most important aspects in regulating plant development (Ballare, 1999). Plants grown under dense canopies or at high density (i.e. shaded conditions) perceive a decrease in the ratio of R to FR light (R:FR ratio). This change in light quality serves as a warning of competition, triggering a series of responses known collectively as the shade avoidance syndrome or shade avoidance reactions (Smith and Whitelam, 1997; Devlin et al., 2003). The reactions in plants induce a rapid and dramatic increase in the extension growth of stems and petioles at the expense of leaf growth, storage organ production, and reproductive development (Table 1). Prolonged shade causes dramatically accelerated flowering, reduced seed sets, and immature fruits. The shade avoidance reactions are mediated predominantly by phytochromes (Smith and Whitelam, 1997). Phytochromes respond to the R:FR ratio as an indicator of proximity to and shade from neighbors. Since blue and red lights are selectively absorbed by chlorophylls for photosynthesis, far-red light is relatively enriched in shaded conditions (FIG. 1B). Thus, shade is represented as a low R:FR ratio. The enriched far-red light signal is recognized by phytochromes as a change in photoequilibrium between Pr and Pfr. The photoequilibrium of phytochrome is represented by the ratio [Pfr]/[Ptot], where [Ptot]=[Pr]+[Pfr]. The lowered R:FR ratio induces a decrease in the Pfr form of phytochromes, which trigger the shade avoidance reactions in plants.

TABLE 1

Shade avoidance reactions in plants.

| Physiological process | Response to shade |
|---|---|
| Germination | Retardation |
| Extension growth | Acceleration |
| Leaf development | Retardation |
| Chloroplast development | Retardation |
| Branching | Retardation |
| Flowering | Acceleration |
| Storage organ deposition | Severe reduction |

In monocultures of crop plants in close proximity, competition for light is an important factor in determining crop yields, because it induces shade avoidance reactions such as elongation of internodes and petioles, inhibition of leaf expansion and growth, retardation of chloroplast development, and early flowering. Since the shade avoidance reaction re-distributes energy and resources to unnecessary elongation and acceleration of senescence (FIG. 2), it cause drastic reduction in products such as leaves, storage organs and seeds. The overexpression of phytochromes in crop plants has been used to overcome these losses from shade avoidance reactions (Robson et al., 1996; Robson and Smith, 1997). FR light is enriched in the shade (See FIG. 1), so the R:FR ratio is decreased. Phytochrome B (phyB) perceives the low R:FR ratio and rapidly induces shade avoidance reactions (Robson et al., 1993). Phytochrome A (phyA) has an antagonistic function to phyB in shade avoidance reactions (Botto et al., 1996). Thus, the *Avena* (oat) phyA gene has been introduced into crop plants such as tobacco, tomato, potato and wheat (Boylan and Quail, 1989; Heyer et al., 1995; Robson et al., 1996; Sineshchekov et al., 2001; Shlumukov et al., 2001). When constitutively expressed, the *Avena* phyA increases shade tolerance, resulting in improvements of leaf expansion and growth without the expense of elongation growth. Consequently, *Avena* phyA-overexpressing tobaccos showed shortened stature in low R:FR and proximity-conditional dwarfism in dense culture. The harvest index of transgenic tobacco showed approximately 20% improvement in leaf product (Robson et al., 1996). Also, transgenic tomatoes, potatoes and wheat displayed suppression of shade avoidance with improved leaf expansion and growth, greening and increased harvest indices of storage organs or seeds (Boylan et al., 1991; Heyer et al., 1995; Shlumukov et al., 2001).

The increase of shade tolerance by overexpression of phytochromes is limited because of the limitation of expression levels and also the degradation of phytochrome proteins upon light illumination. Theoretically, an increase in Pfr under low R:FR ratios could mediate shade tolerance in plants. Thus, spectral phytochrome mutants that absorb longer wavelengths (i.e. bathochromic or red-shifted mutants in Pr absorption maxima) can be used to confer shade tolerance on plants. As shown in FIG. 3, the simulated spectra of Pr in bathochromic mutants shows an increase in the area overlapping with the shade spectrum, in which phytochromes recognize shade like red light and can be transformed to more Pfr form. Consequently, a shift of photoequilibrium to Pfr would overcome the shade avoidance. The absorption spectra of the phytochromes overlapped with the shade spectrum and the red-shifted mutants had greater overlap than the wild-type or blue-shifted mutant (FIG. 3). The overlap of the 8 nm and 12 nm red-shifted mutants increased to 153±4% and 176±4% respectively, whereas the 8 nm blue-shifted mutant decreased to 67±4%. These calculations suggest that the red-shifted mutant can absorb more light in the shade, and maintain an increased amount of biologically active Pfr compared to wild-type phyA, thus conferring shade tolerance to plants. Thus, bathochromic phytochromes in this invention can be practically applied to suppress shade avoidance reactions under shaded conditions such as canopy and proximity cultures, which increase shade tolerance to plants with high yields. The plants referred to here are those economically important in agriculture and horticulture. As used herein, the term "economically important higher plants" refers to higher plants that are capable of photosynthesis and widely cultivated for commercial purpose. The term "plant cell" includes any cells derived from a higher plant, including differentiated as well as undifferentiated tissues, such as callus and plant seeds.

SUMMARY OF THE INVENTION

The present invention relates to nucleic acid molecules encoding modified phytochrome A (phyA) protein of which Pr absorption spectra have been shifted to longer wavelength (i.e. bathochromism or red-shift). Such nucleic acid molecules confer shade tolerance to plants. Since the shade avoidance is second only to disease as a cause of crop-yield losses, the suppression of shade avoidance can significantly increase the crop yields. In this invention, several bathochromic phytochromes were developed and characterized photochemically and their biological functions were demonstrated by using transgenic Arabidopsis plants. The developed bathochromic phytochromes confer shade tolerance to plants: 6 nm bathochromic mutant (Red-6) had an increased shade tolerance of approximately 220% and 8 nm bathochromic mutant (Red-8) increased to approximately 270%, whereas 8 nm hypsochromic mutant (Blue-8) displayed a decreased shade tolerance. There is a proportional relationship between shade tolerance and wavelength shift in the absorption spectrum of the phytochrome. This means that the magnitude of the red shift is strongly correlated to level of shade tolerance. In this invention, 12 nm bathochromic mutant was developed. Therefore, this invention relates the development of bathochromic phytochromes and their application to develop shade-tolerant plants with high-yields.

DETAILED DESCRIPTION OF THE INVENTION

Figure 1:
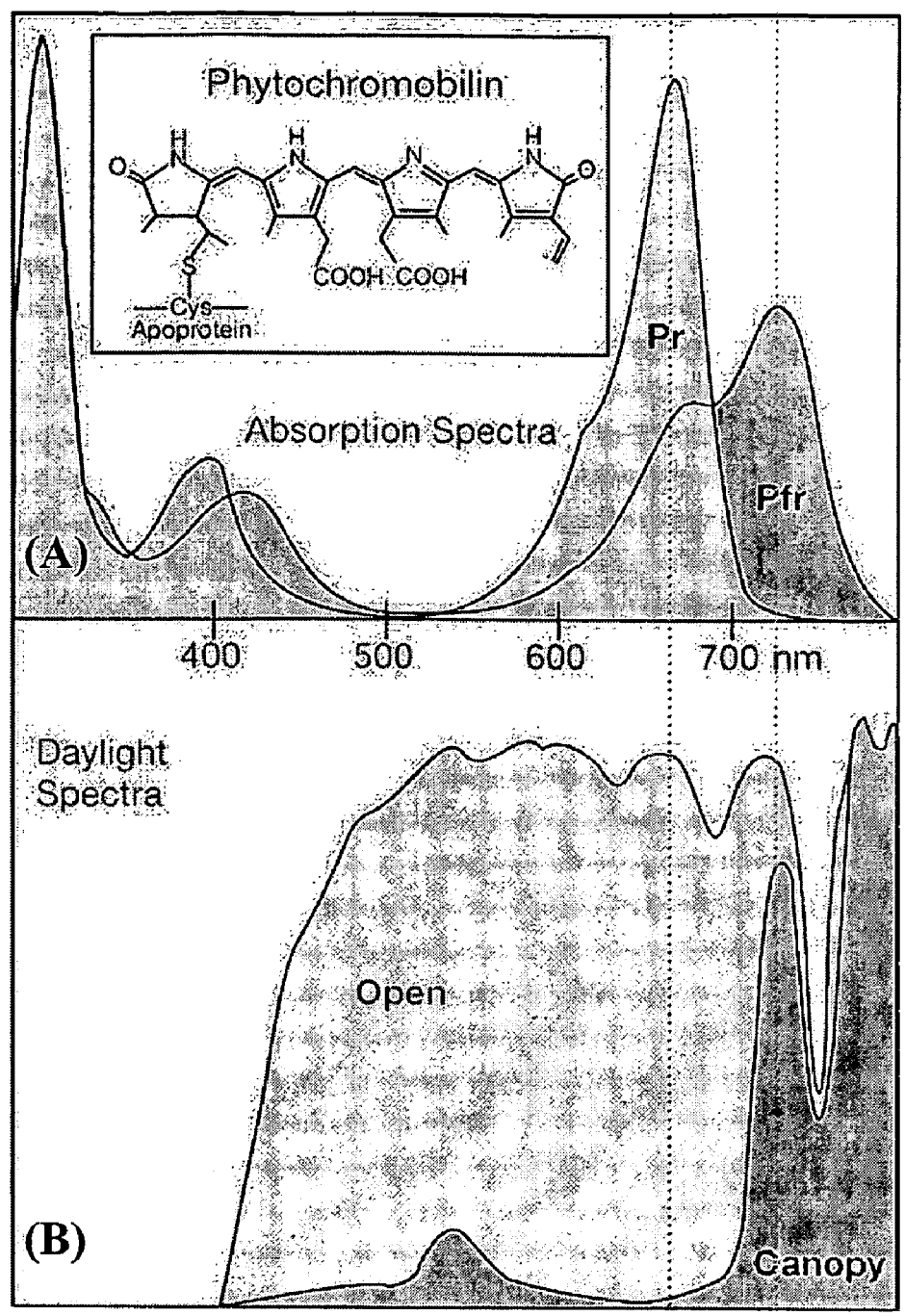
FIG. 1 shows absorption spectra of phytochromes (A) and daylight spectra in open and canopy covered areas (B). In the canopy, only far-red light is enriched, which induces shade avoidance reactions in plants. [from Smith, 2000]
Figure 2:
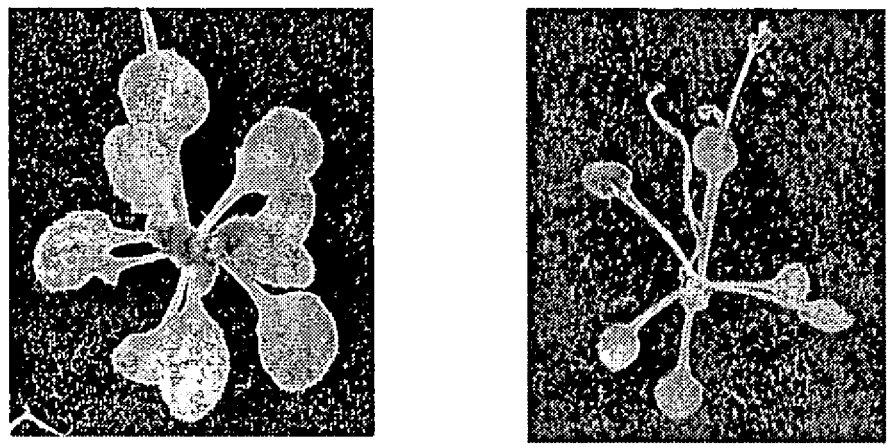
FIG. 2 shows the phenotypes of Arabidopsis plants caused by shade avoidance. In high R:FR ratios, the relative [Pfr] is increased and shade avoidance responses are suppressed, including inhibition of stem elongation and flowering. A reduced R:FR ratio causes photoconversion from Pfr to Pr and the relative [Pfr] is decreased, which induces shade avoidance reactions.
Figure 2:
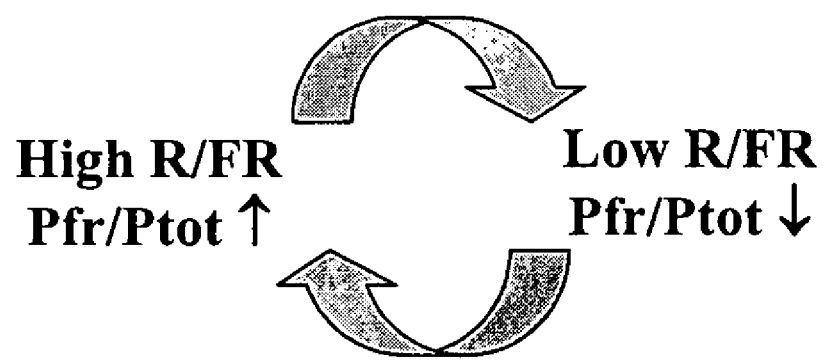
Figure 3:
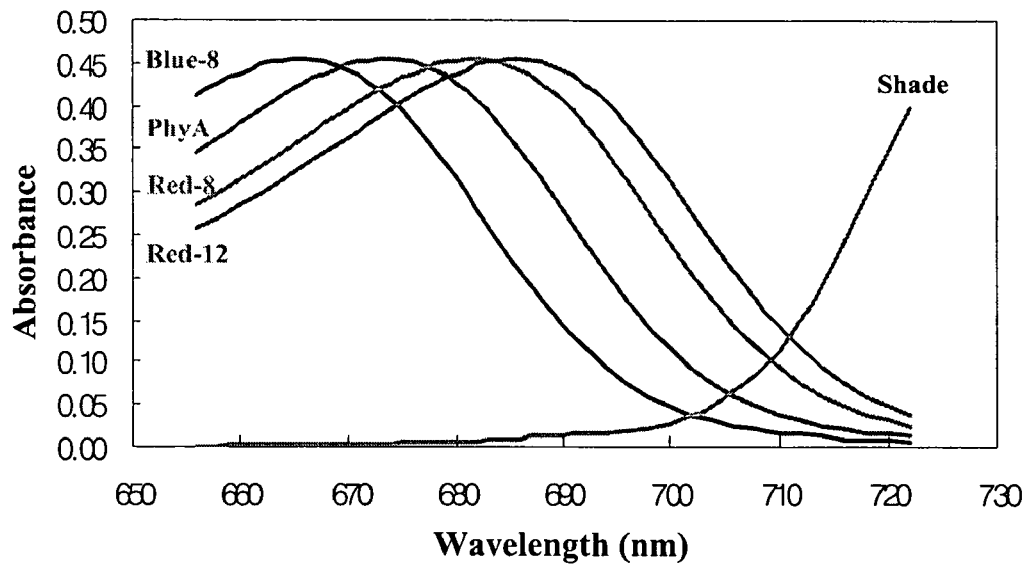
FIG. 3 shows simulated spectra of Pr in 8 nm blue-shifted (Blue-8), 8 nm red-shifted (Red-8), and 12 nm red-shifted (Red-12) spectral mutants and overlaps of these spectra with the shade spectrum of the LED growth chamber. Each red-shifted mutant shows an increase in area of the spectrum which overlaps with shade. The changes in area of overlap were calculated relative to the overlap between wild-type phyA (phyA) and shade (100%). The 8 nm red-shifted phyA overlap was 153±4%, whereas the 8 nm blue-shifted phyA overlap was 67±4%. The 12 nm red-shifted phyA showed greater increase than the 8 nm-shifted mutant (176±4%). These values can also reflect the changes in photoequilibrium.

Phytochromes are dimeric chromopeptides (monomer sizes of 120~130 kDa) that carry the chromophore phytochromobilin (PΦB), which is covalently linked to a cysteine residue on each peptide via a thioether linkage. *Avena* (oat) phyA consists of 1129 amino acids and the chromophore is attached at Cysteine 322 (Cys322 or C322). To generate absorption wavelength-shifted phyA mutants, bathochromic (shifted to longer wavelength, red-shifted) or hypsochromic (shifted to shorter wavelength, blue-shifted), the interactions between the chromophore and the surrounding amino acid residues in the chromophore-binding region were modified by site-directed mutagenesis. Approximately 30 candidate sites including 18 ring-bearing amino acids were selected and changed to another amino acid by site-directed mutagenesis. The full-length mutant phytochromes were expressed in the *Pichia* protein expression system, assembled with chromophore, phytochromobilin (PΦB), and their photochemical properties were analysed by using spectrophotometers. From these analyses, several absorption wavelength-shifted mutants were obtained (Table 2): two 2 nm hypsochromic, one 8 nm hypsochromic, three 2 nm bathochromic, four 4 nm bathochromic, six 6 nm bathochromic, two 8 nm bathochromic, one 10 nm bathochromic, and one 12 nm bathochromic mutants (total 3 hypsochromic and 17 bathochromic mutants).

TABLE 2

Absorption wavelength-shifted mutants in this invention.

| Photochemical characteristics | Spectral change | Mutation | Remark |
|---|---|---|---|
| Bathochromic shift | +2 | D308K (SEQ ID NO: 11) | Red-shifted |
| | +4 | Y263F (SEQ ID NO: 12) | |
| | | F307W (SEQ ID NO: 13) | |
| | | Y326F (SEQ ID NO: 14) | |
| | +6 | Y385A (SEQ ID NO: 1) | |
| | | Y385F (SEQ ID NO: 2) | |
| | | Y385V (SEQ ID NO: 3) | |
| | | Y385W (SEQ ID NO: 4) | |
| | | F389A (SEQ ID NO: 5) | |
| | | Y385W/F389A (SEQ ID NO: 6) | |
| | +8 | F389Y (SEQ ID NO: 7) | |
| | | F307R/C371A (SEQ ID NO: 8) | |
| | +10 | F307R/C371A/Y385W/F389A (SEQ ID NO: 9) | |
| | +12 | F307W/Y385A/F389A (SEQ ID NO: 10) | |
| Hypsochromic shift | −2 | S310V (SEQ ID NO: 15) | Blue-shifted |
| | −8 | R317E (SEQ ID NO: 16) | |

Figure 4:
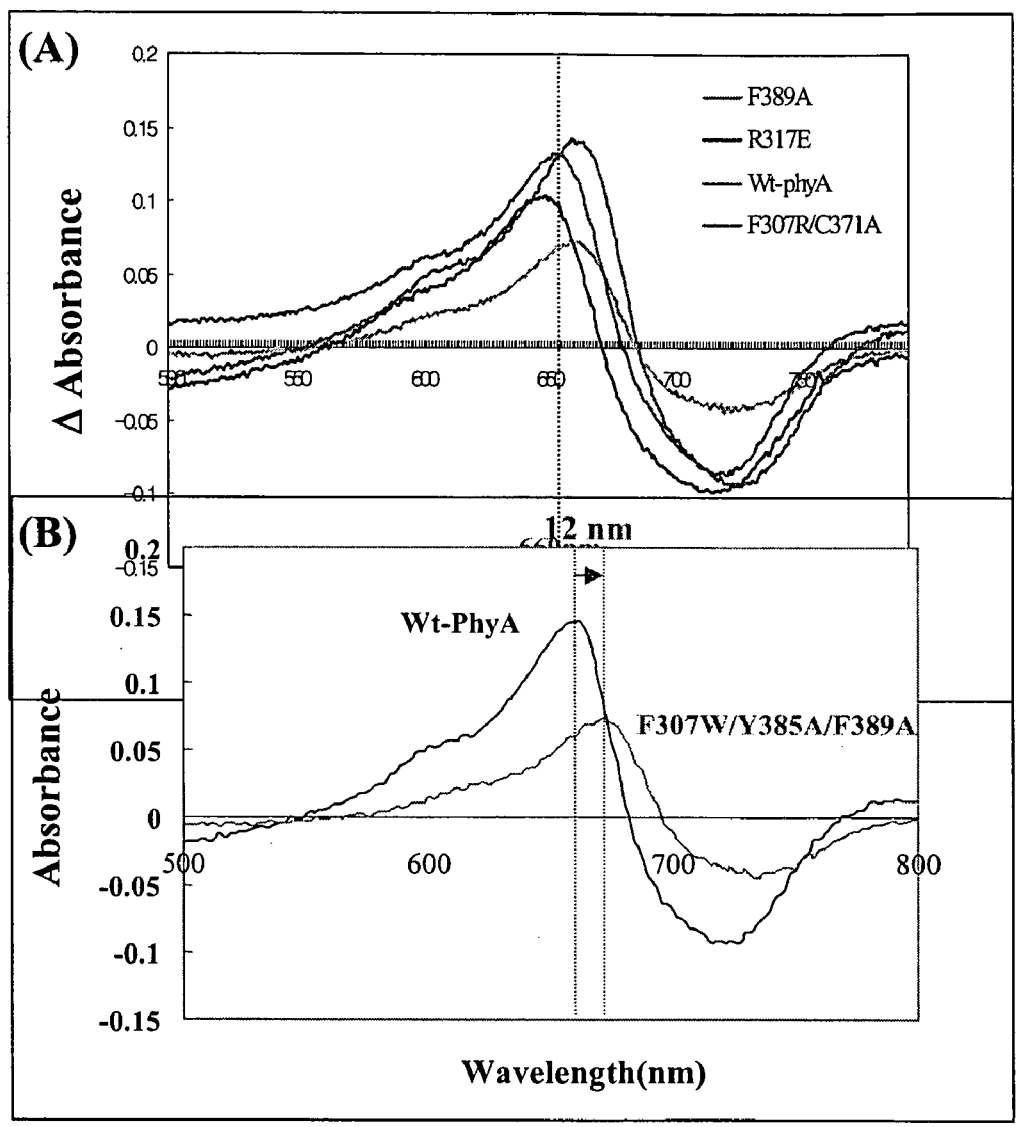
FIG. 4 shows difference spectra of wavelength-shifted mutant phytochromes assembled with PΦB. (A) with 8 nm blue-shifted (R317E), 6 nm red-shifted (F389A), and 8 nm red-shifted (F307R/C371A) mutants. (B) with 12 nm red-shifted mutant (F307R/Y385A/F389A) that showed maximally red-shifted absorption spectrum. Wt-PhyA, wild-type recombinant phyA. Gray lines show Pr peaks.

Several absorption wavelength-shifted mutant proteins were assembled with chromophores and purified for further analyses. The difference spectra of several mutants were shown in FIG. 4, including 8 nm hypsochromic R317E mutant, 6 nm bathochromic F389A mutant, 8 nm bathochromic F307R/C371A double mutant, and 12 nm bathochromic F307W/Y385A/F389A triple mutant. Thus, several bathochromic phytochromes were successfully developed by site directed mutagenesis in the chromophore-binding region.

Phytochromes manage a variety of photomorphogenic responses to the red/far-red region of spectrum (R/FR). Particularly, seed germination and shade avoidance are unique R/FR light responses regulated by phytochromes (Botto et al., 1996; Smith and Whitelam, 1997; Ballare, 1999; Sullivan and Deng, 2003). Light responses by phytochromes showed a positive correlation with the concentration of Pfr forms, [Pfr]. The initiation of shade avoidance reactions is determined by a dynamic photoequilibrium of phytochrome, and the photoequilibrium of phytochrome is represented by the ratio [Pfr]/[Ptot], where [Ptot]=[Pr]+[Pfr]. Even though enough photosynthetically active radiation may exist in the surroundings of a plant, the enriched and reflected FR from neighbors or leaves lowers the ratio of R:FR (See FIG. 1). The lowered R:FR ratio induces a decrease in the Pfr form of phytochromes. Thus, bathochromic phytochromes in which Pr absorption spectra have been shifted to longer wavelength can absorb more light even in the low R:FR, which suppresses shade avoidance in plants. In this invention, several wavelength-shifted phyA mutants were selected and transformed into phyA-deficient *Arabidopsis thaliana* (phyA-211) to investigate the in vivo function of the mutants, especially under shaded conditions. Among the wavelength-shifted mutants listed in Table 2, R317E was selected as the representative blue-shifted mutant (8 nm), and F389A and F307R/C371A as representative red-shifted mutants, 6 nm and 8 nm shifts, respectively. Phenotypic characterization of the transgenic plants was performed to identify features positively correlated with the change in absorption spectra and the tolerance of shade avoidance. In addition, since the shade avoidance is second only to disease as a cause of crop-yield losses, the suppression of shade avoidance (i.e. shade tolerance) by using red-shifted phytochromes will have potential for biotechnological applications, for example increase of crop yields by suppressing shade avoidance, and increase in the value of decorative plants such as turfgrass.

Figure 5:
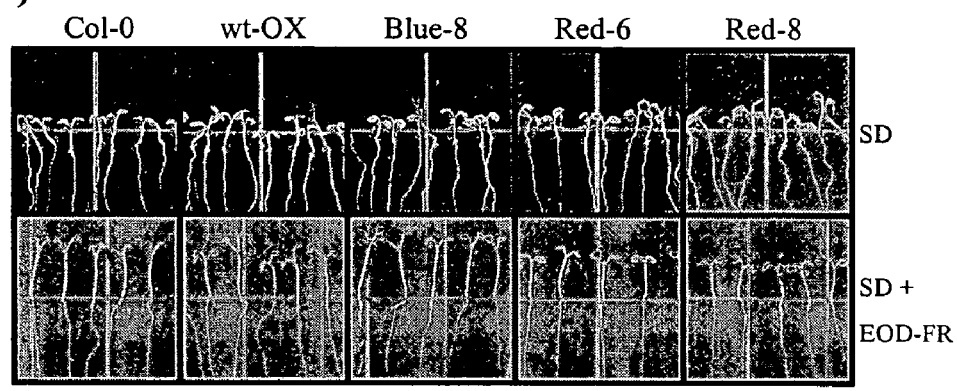
FIG. 5 shows the effects of wavelength-shifted phytochromes on hypocotyl elongation in seedlings under shade. Around 30 individual 6-day-old transgenic and control seedlings were used to measure hypocotyl elongation. SD, short day (8 hrs: 16 hrs=light: dark); EOD-FR, end of day far-red light (15 min treatment of FR, 10 μmole/m$^2$·s). (A) Representative phenotypes in control and transgenic seedlings under SD or SD+EOD-FR condition. (B) Relative sensitivity of wavelength-shifted phyA in seedlings in the shade, as indicated by hypocotyl lengths in seedlings grown under SD+EOD-FR. Sensitivity (%)=(average of hypocotyl lengths of each plant/average of hypocotyl length of Col-0)×100.
Figure 5:
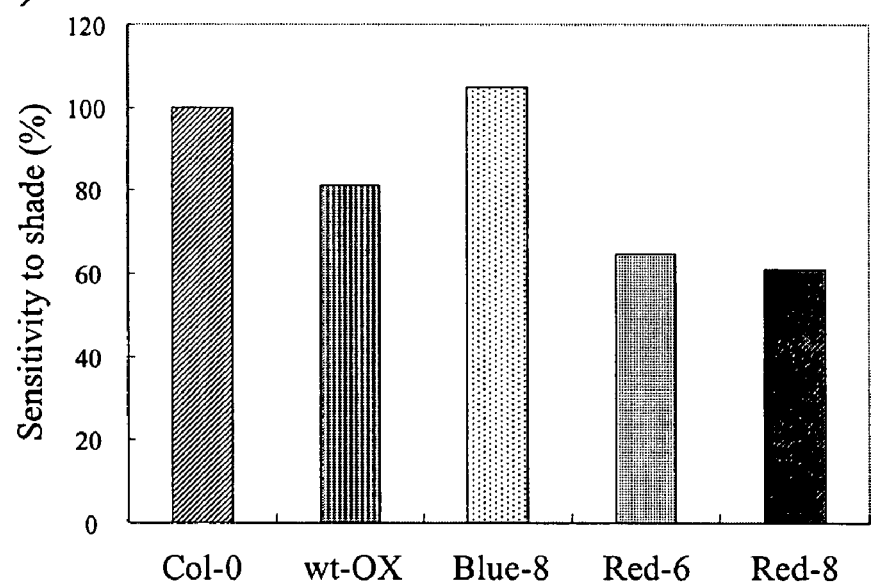

Shade avoidance reactions in plants induced by low R:FR ratios (i.e. shade) stimulate petiole elongation, retardation of leaf expansion, and floral induction (Morelli and Ruberti, 2000; Delvin et al., 2003). Additionally, hypocotyl elongation is very sensitive to light conditions: therefore the hypocotyl lengths of transgenic plants were tested. In these experiments, the R:FR ratio was modified by adding a far-red light period at the end of the day (EOD-FR) or by mixing the far-red light with white light irradiance (far-red light supplemented white light). To compare shade tolerance in seedlings, wild-type and transgenic seedlings were grown in 16-h light/8-h dark (long-day, LD) cycles for 3 days prior to growth for 3 days under 8-h light/16-h dark (short-day, SD) cycles, with or without a 15 min EOD-FR treatment. The wt-OX seedlings showed shorter hypocotyl lengths than non-transgenic wild-type seedlings (Col-0) with the EOD-FR treatment (FIG. 5A). The Blue-8 transgenic seedlings showed a hypersensitive phenotype to shade, compared to Col-0. The two transgenic seedlings with red-shifted phyA displayed less hypocotyl elongation than Col-0 and wt-OX. Red-8 plants reduced the shade sensitivity approximately 35% compared to Col-0 (FIG. 5B). In comparison, Blue-8 plants displayed approximately 10% increased shade sensitivity compared to Col-0. These results suggested that the red-shifted phyA could confer shade tolerance in seedlings, while the blue-shifted mutant confer shade sensitivity.

Figure 6:
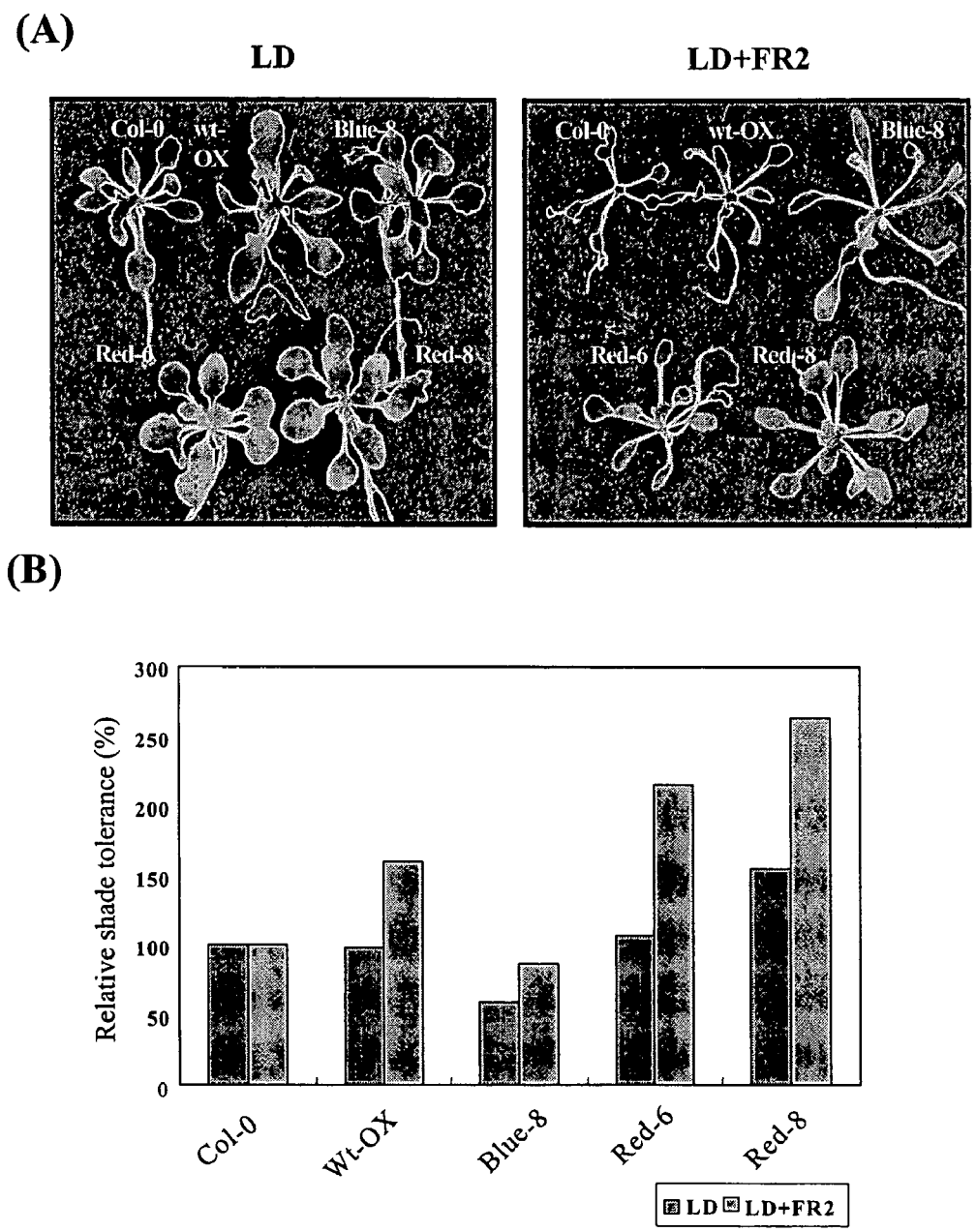
FIG. 6 shows representative phenotypes (A) and comparison of shade tolerance (B) of adult transgenic plants incubated in shade conditions. LD, long day (16 hrs: 8 hrs=light: dark); LD+FR2, W:FR=60 μmole/m$^2$·s:10 μmole/m$^2$·s; W, white light. wt-OX, oat phyA-overexpressing transgenic plant; Blue-8, 8 nm blue-shifted R317E transgenic plant; Red-6, 6 nm red-shifted F398A transgenic plant; Red-8, 8 nm red-shifted F307R/C371A transgenic plant. Relative shade tolerance (%)={(ratio of leaf area/petiole length of each transgenic plant)/(ratio of leaf area/petiole length of Col-0)}×100.

To investigate the effects of bathochromic phytochromes in the shade avoidance responses in adult plants, transgenic plants were grown in a long day (LD) cycle for two weeks and transferred to white light with supplementary far-red light conditions in a LED (light emitting diode) growth chamber (FIG. 6A). Since shade avoidance responses are represented as complex changes in phenotypes including elongation of petioles and hypocotyls, retardation of leaf growth, and floral induction in *Arabidopsis*, these phenotypes were investigated with the transgenic plants of wavelength-shifted phyA mutants. The ratio of leaf area to petiole length is influenced by light quality. In the shade, leaves are smaller and petioles are longer than under high R:FR. Therefore, changes in the ratio of leaf area/petiole length can be a measure of shade tolerance. Relative shade tolerance was calculated as shade tolerance (%)={(leaf area/petiole length of transgenic plant)/(leaf area/petiole length of Col- 0)}×100. Wt-OX plants showed 150% increase in shade tolerance (FIG. 6B), reflecting the increased protein stability of monocot (*Avena*) phyA in dicot (*Arabidopsis*) plants, as well as higher expression levels of phyA under the constitutive promoter. Red-6 had an increased shade tolerance of approximately 220% and Red-8 increased to approximately 270%, whereas Blue-8 displayed a decreased shade tolerance (i.e. hypersensitive to shade). These data indicate that there is a proportional relationship between shade tolerance and wavelength shift in the absorption spectrum of the phytochrome in leaf morphology.

In the shade, most blue and red light is reflected or absorbed by leaves and far-red light is enriched. Under these conditions, phyA accelerates floral induction by inhibiting the phyB-mediated suppression of flowering (Hayama and Coupland, 2003; Cérdan and Chory, 2003). Therefore, it is predicted that transgenic plants with red-shifted phyA would delay the shade-induced flowering. The results indicate that the red-shifted mutants displayed late floral induction in low R:FR (supplementary far-red light), compared to Col-0, whereas the blue-shifted mutant had little affect on floral induction (Table 3). Thus, the red-shifted phytochromes induced a delay in floral induction, supporting that phyA recognizes the low R:FR (i.e. shifts the photoequilibrium of Pr:Pfr) and induces flowering. The amount of Pfr in the transgenic of red-shifted mutants is relatively higher than that in the transgenic of wt-OX or Col-0, and this delayed initiation of flowering in red-shifted mutants, whereas initiation of flowering was slightly accelerated in the blue-shifted mutant.

TABLE 3

Effect of wavelength-shifted phytochromes on flowering in shade

|  | White | White + FR |
| --- | --- | --- |
| Col-0 | 9.83 ± 0.83 | 6.42 ± 0.49 |
| Wt-OX | 9.50 ± 0.50 | 6.82 ± 0.37 |
| Blue-8 | 9.08 ± 0.75 | 6.25 ± 0.72 |
| Red-6 | 9.92 ± 0.49 | 7.92 ± 0.64 |
| Red-8 | 10.2 ± 0.68 | 8.83 ± 0.37 |

Data are number of rosette leaves at bolting. White light (60 μmole/m$^2$), FR (10 μmole/m$^2$ · sec).
They were cultured in plastic boxes to maintain humidity in the LED growth chamber.

Figure 7:
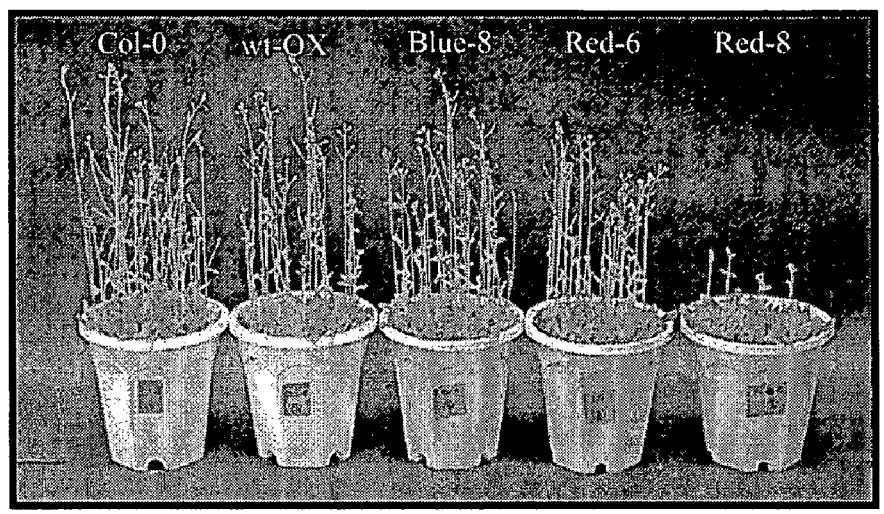
FIG. 7 shows the effect of bathochromic phytochromes on proximity responses (A) and the comparison of leaf area under close proximity conditions (B). In A, 40 transgenic or control plants were planted in 10 cm diameter pots and cultured in LD for 6 weeks. wt-OX, oat phyA; Blue-8, R317E; Red-6, F398A; Red-8, F307R/C371A. In B, transgenic and control plants were planted at densities of 6 or 40 plants per 10 cm diameter pots and cultured in LD for 6 weeks. 12 transgenic or control plants were measured.
Figure 7:
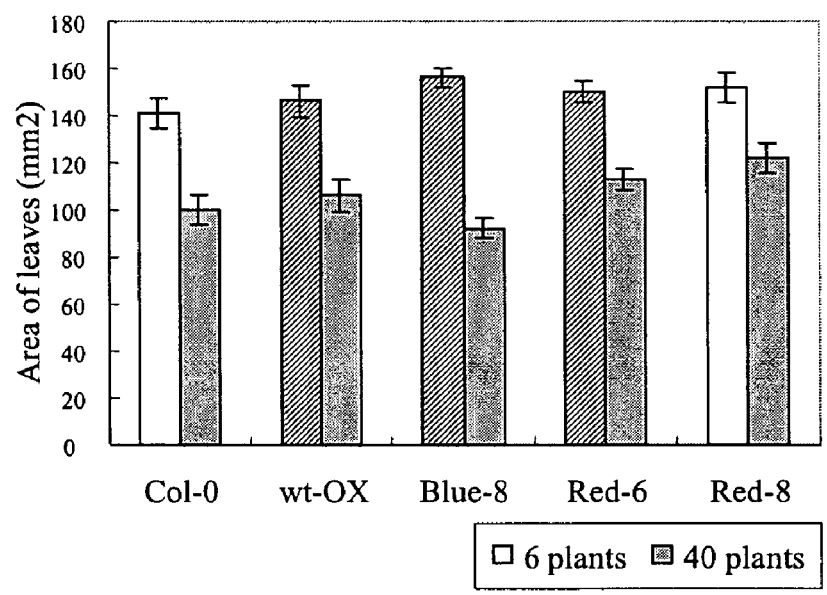

In shade avoidance responses, the plants perceive the relative amounts of red light and undergo changes in photoequilibrium with enriched far-red light (Neff et al., 2000; Gilbert et al., 2001). Shorter wavelengths of light are scattered or absorbed by leaves and longer wavelengths (far-red) are reflected by neighbors and enriched in dense areas, such as deep forests. To compete for light, plants monitor their neighbors by analyzing the R:FR ratio by phytochromes. To measure the response of wavelength-shifted mutants to culture density, synchronized plants at the same developmental stage were transferred to a 10 cm-diameter pot. High-density cultures consisted of 40 plants per pot and control cultures contained 6 plants per pot. All plants were cultured in white light on a long day cycle. In high density cultures, Col-0, wt-OX and Blue-8 plants showed retardation of growth and induced flowering, whereas red-shifted mutants showed a delay in flowering and relatively increased leaf area (FIG. 7A & Table 4). High-density cultures of Red-8 showed over 20% increase in leaf area compared to Col-0, and Blue-8 displayed reduced leaf area compared to Col-0 (FIG. 7B). Col-0 leaf area was similar tendency to the results of the shade experiment. However, the stress of close proximity did not show drastic changes in leaf morphology, compared to shade conditions. Red-shifted mutants in the high-density cultures delayed flowering by approximately two pairs of rosette leaves, compared to Col-0. Red-shifted mutants in the high-density cultures showed almost same flowering time as in the low-density cultures, indicating that the bathochromic phytochromes conferred the tolerance to the floral initiation by the high-density culture.

TABLE 4

Effect of wavelength-shifted phytochrome on flowering in proximity.

|  | 6 plants/pot | 40 plants/pot |
| --- | --- | --- |
| Col-0 | 11.83 ± 0.68 | 8.04 ± 0.76 |
| wt-OX | 11.5 ± 0.5 | 9.68 ± 1.06 |
| Blue-8 | 10.48 ± 0.75 | 8.64 ± 0.98 |
| Red-6 | 11.92 ± 0.49 | 10.14 ± 1.06 |
| Red-8 | 13.2 ± 0.68 | 12.78 ± 0.8 |

Data are number of rosette leaves at bolting.

Overexpression of phytochromes, especially the transformation of monocot phyA into dicot plants, has been used for suppression of shade avoidance reactions, eventually increasing the harvest yields (Robson et al., 1996; Robson and Smith, 1997). The oat phyA gene has been introduced into crop plants such as tobacco, tomato, potato and wheat (Boylan and Quail, 1989; Heyer et al., 1995; Robson et al, 1996; Sineshchekov et al., 2001; Shlumukov et al., 2001). In transgenic tobacco overexpressing oat phyA, the harvest index was increased about 20% (Robson et al., 1996), and transgenic potatoes overexpressing phyB had increased tuber yield and decreased the density effects (Boccalandro et al., 2003). In most transgenic plants, including tomato, potato, and wheat, the overexpression of phytochromes suppresses shade avoidance and promotes improved leaf expansion and growth, greening, and increased harvest index for storage organs or seeds. Therefore, the transgenic approach with phytochrome genes has potential for biotechnological applications, especially for the increase of crop-yields by reducing losses due to shade avoidance reactions. In this invention, bathochromic phytochromes have been developed by site-directed mutagenesis and it has been demonstrated that transgenic plants with bathochromic phytochromes possess improved shade tolerance. Furthermore, the magnitude of the red shift was strongly correlated to level of shade tolerance: an 8 nm red-shifted mutant showed more shade tolerance than a 6 nm red-shifted mutant (270% vs. 220% compared to Col-0). This means that the combination mutants with a 10-12 nm red shift can suppress the shade avoidance reactions more strongly than mutants with a 6-8 nm shift. These results suggest that the biological function of phytochromes is directly related to its photo-chemical properties and the more red-shifted a phyA mutant, the greater the shade tolerance it confers. In comparison, the blue-shifted mutant resulted in increased shade sensitivity. The results in this invention demonstrate that altered phytochromes will be an important tool for plant biotechnology. Since shade avoidance is one of major causes to induce crop-yield losses, introducing the red-shifted phytochromes into crop plants could prevent substantial losses in crop yields. Furthermore, decorative plants such as turfgrass could be improved. The transgenic turfgrass would be shorter and greener in the shade, thus increasing the decorative value. Therefore, this invention enables us to develop shade tolerant plants with high yields and values.

EXAMPLES

All chemical reagents used were purchased from Sigma (St. Louis, Mo.) unless specified otherwise. Restriction and modifying enzymes were obtained from New England Biolabs, Inc. (Beverly, Mass.) and Roche Molecular Biochemicals (Indianapolis, Ind.). GENEEDITOR™ in vitro Site-Directed Mutagenesis System, a machine for preparing site-directed mutagenesis, was purchased from Promega (Madison, Wis.). All polymerase chain reactions (PCR) were performed using high fidelity DNA polymerase, TURBO® Pfu polymerase, a polymerase made by Strategene, which was purchased from Stratagene (La Jolla, Calif.). For the expression of all recombinant phytochromes, the Pichia pastoris protein expression system from Invitrogen (Carlsbad, Calif.) was used.

Generation of Wavelength-Shifted phyA Mutants by Site-Directed Mutagenesis

To perform site-directed mutagenesis in Avena (oat) phyA, a full-length phytochrome gene was subcloned into pGEM-11zf(+) (Promega, Medison, Wis.) from pFY122 (Boylan and Quail, 1989) by digesting with BamHI and EcoRI. To create Kozak sequence (accatgg) in the construct for protein expression in Pichia, PCR amplification was performed with a forward primer, 5'-cgggatccaccatggcttcct-caaggcctgcttcc-3'(underlined, BamHI) (SEQ ID NO: 17), and a reverse primer, 5'-cgcccgggctgcagagc tagatatagcatc-3'(underlined, SinaI) (SEQ ID NO: 18). The amplified PCR products were digested with BamHI and AvrII, and replaced with the corresponding fragments of wild-type phyA in pGEM-11zf(+). The clones were confirmed by DNA sequencing. The site-directed mutagenesis was performed by using either a GENEEDITOR™ in vitro site-directed mutagenesis system (Promega, Medison, Wis.), a machine for preparing site-directed mutagenesis, or a QUICK-CHANGE™ kit (Stratagene, La Jolla, Calif.), a kit for preparing site-directed mutagenesis, according to the manufacturer's recommendations. Mutagenic primers with base substitutions used in this study were listed in Table 5. To be convenient for screening, a proper restriction site was generated into each mutagenic primer or removed from original restriction site. The mutagenized plasmids were confirmed by restriction and DNA sequencing.

Phytochrome Constructs for Recombinant Protein Preparations

Full-length oat phyA was first subcloned into the pASK75 vector to attach a streptavidin affinity tag (strep-tag) at the end of the gene as described (Kim et al., 2004). Prior to the subcloning of phyA gene, the pASK75 vector was modified to have a NotI restriction site at the end of the strep-tag for further subcloning into Pichia expression vector, pPIC3.5K (Invitrogen, Carlsbad, Calif.). The strep-tag is composed of ten amino acids and strongly binds to streptavidin protein, which is used for affinity chromatography with streptavidin agarose (Sigma, St. Louis, Mo.). Specific primers for PCR amplification were designed to make an in frame construct with the strep-tag, 5'-cg ggatccaccatggcttcctcaaggcctgcttcc-3' (forward, BamHI) (SEQ ID NO: 17) and 5'-tcgcgtcgacttgtcccattgctgttggagc-3' (reverse, SalI) (SEQ ID NO: 19). After confirmation of the constructs by restriction map analysis and DNA sequencing in pASK75, the phyA gene was subcloned into the pPIC3.5K vector using BamHI and NotI for the protein expression in Pichia pastoris. To subclone mutant phytochromes, 1.6 kb of fragments (BamHI and AvrII) in wild-type phyA gene were exchanged with the fragments of each phyA mutant digested by the same restriction enzymes. After the phyA mutant genes were subcloned into pPIC3.5K, they were all confirmed by DNA restriction map analysis and DNA sequencing.

TABLE 5

Mutagenic primers used for this invention.

| Mutagenic site | Mutants | Restriction enzyme | Mutagenic primer sequence |
|---|---|---|---|
| Y263 | Y263F | Stu I (X) | ggtcttgagcctttcttggactgcactatcc (SEQ ID NO: 20) |
| S296 | S296A | BssH II | gattgccgtgcgcgcgccataaaaggtc (SEQ ID NO: 21) |
| F307 | F307R | Sac II | gaggcactcccgcgggatattagcctatg (SEQ ID NO: 22) |
|  | F307W | Nco I | gctgaggcactcccatgggatattagcctatgtgg (SEQ ID NO: 23) |
| D308 | D308K | DraI | gcactccccttaaaatttgcctatgtg (SEQ ID NO: 24) |
| S310 | S310V | EcoRV | ctccctttgatatcgtcctatgtggttcag (SEQ ID NO: 25) |
| S314 | S314L | Nhe I | gcctatgtgggctagcactcagggcac (SEQ ID NO: 26) |
| R317 | R317E | XhoI | ggttcagcactcgaggcaccacacag (SEQ ID NO: 27) |
| Y326 | Y326F | Pst I | cagttgtcacctgcagtttatggagaacatg (SEQ ID NO: 28) |
| W366 | W366F | N.A. | gaagaaactattcggcctccttg (SEQ ID NO: 29) |
| C371 | C371A | AviII | ggcctccttgttgcgcaccatgagagc (SEQ ID NO: 30) |
| Y385 | Y385A | Sph I | ccgctgcgtgctgcatgcgagttcttagcacag (SEQ ID NO: 31) |
|  | Y385F | Sph I | ccgctgcgttttgcatgcgagttcttagcac (SEQ ID NO: 32) |
|  | Y385V | Sph I | ccgctgcgtgttggcatgcgagttcttagcacag (SEQ ID NO: 33) |
|  | Y385W | Sph I | ccgctgcgttgggcatgcgagttcttagcacag (SEQ ID NO: 34) |
| F389 | F389A | Stu I | gttatgcttgtgaggccttagcacaggtg (SEQ ID NO: 35) |
|  | F389Y | Sca I | gttatgcttgtgagtacttagcacagg (SEQ ID NO: 36) |
| F307/C371 | F307R/C371A | SacII/AviII | gaggcactcccgcgggatattagcctatg (SEQ ID NO: 37) |
|  |  |  | ggcctccttgttgcgcaccatgagagc (SEQ ID NO: 38) |

Cf. N.A., not applicable;
bold, created restriction enzyme sites;
(X), abolished original restriction site Isolation and Purification of Chromophores Phytochromobilin (PΦB) and phycocyanobilin (PCB) were used as the chromophores for holo-phytochrome assembly in this work. PΦB was extracted from red algae, Porphyridium cruentum by methanolysis and subsequently purified by chromatography as followed previous report (Beale and Cornejo, 1991). Porphyridium cruentum cells were grown in minimal liquid medium at 27° C. under cool white and red fluorescent lights (1:1 ratio). The culture medium was aerated by magnetic stirring and continuous flushing with an air/$CO_2$ gas mixture. The harvested cells were washed with acetone until the supernatant was colorless. Then, the pellet was resuspended with 1 mg of $HgCl_2$ in 1 ml of the absolute methanol and incubated in darkness for 16-24 hours at 40° C. After methanolysis, the supernatant was applied to a C-18 Sep-Pak column (Waters—Millipores, Mass.), and washed with 0.1% trifloric acid (TFA) in distilled water. PΦB was fractionated with acetonitrile/0.1% TFA (60:40, v/v). The fraction containing PΦB can be detected at 370 nm. Phycocyanobilin (PCB) was purified from lyophilized *Spirulina platensis* powder purchased from Sigma. The lyophilized powder was resuspended into water and centrifuged to get supernatant. The supernatant was mixed with trichloroacetic acid (1%, w/v), and followed the methanolysis. It can be detected at 370 nm. The concentration of PCB and PΦB was determined by absorption spectroscopy in HCl (2%)/methanol, using extinction coefficients (ε) of 37,900 $M^{-1}$ $cm^{-1}$ at 690 nm for PCB and 64,600 $M^{-1}$ $cm^{-1}$ at 708 nm for PΦB, respectively. The purified pigments were dissolved in dimethyl sulfoxide (DMSO), wrapped with foil and stored at −80° C. until use.

Expression and Purification of Mutant Phytochromes

The pPIC3.5K constructs with the mutated phytochrome genes were transformed into *Pichia pastoris* GS115 cells by electrophoration method, as previously described (Kim et al., 2004). This expression vector has two selective markers, histidine auxotrophic marker and geneticin (G-418) resistant marker. First, the transformants were selected on minimal media containing dextrose (MD, 0.34% yeast nitrogen base, $4\times10^{-5}$% d-biotin, 2% dextrose) media plates to remove non-transformants. Then, the selected colonies from MD medium were spread out on yeast extract-peptone-dextrose (YPD, 1% yeast extract, 2% bactopeptone, 2% dextrose) agar plates containing 3 mg/mL of geneticin antibiotics to select out the *Pichia* transformants bearing multi-copy integrated phytochrome expression cassettes in the genomic DNA for protein expression. For the induction of proteins, the selected cells were grown on 5 mL of minimal medium containing methanol (MM, 1.34% yeast nitrogen base, $4\times10^{-5}$% d-biotin, 1% methanol) at 30° C. with shaking at 250 rpm overnight, transferred to 100 mL of minimal medium containing glycerol (MGY, 1.34% yeast nitrogen base, $4\times10^{-5}$% d-biotin, 1% glycerol) and cultured one more day until it reached 5.0 of optical density at 600 nm. The grown cells were harvested and transferred to 500 mL of MM media in 2 L of a baffled flask for the protein induction (the optical density to 0.8~1.0). Then, the cells were cultured for 20-24 hours at 30° C. with shaking at 250 rpm for the protein induction. Cultured cells were harvested by centrifugation (4500 rpm, 5 min at 4° C.) and washed with 50 mL of sterilized water. The washed cell pellets were resuspended with 10 ml of TE buffer (100 mM Tris-HCl, pH 8.0, 1 mM EDTA) containing protease inhibitors, including 1 mM phenylmethyl-sulfonyl fluoride (PMSF), 4 μg/mL leupeptin and 4 μg/mL pepstatin. Resuspended *Pichia* cells were homogenized in liquid nitrogen with a homogenizer (Nihonseiki Kaisha, Japan; model AM-5) for 5 min at 13,000 rpm twice. The disrupted cell extracts were centrifuged at 15,000 rpm for 20 min under 4° C. The supernatants containing the apo-phytochromes were precipitated with ammonium sulfate (0.23 g/ml) to fractionate from cell extract contaminants. The re-solublized precipitants in TE buffer were directly used for in vitro chromophores-adduct. The purified chromophores, PCB or PΦB was added to each supernatant at a final concentration of 20 μM and stood on ice for 1 hr under the dark. For the protein purification, chromophore-adducted samples were dialyzed for 2 hrs under dark at 4° C. to remove excessive salts from the samples. The dialyzed samples were passed through a 0.45 μm microfilter (Nalgene) to remove any insoluble particles and loaded onto streptavidin-affinity column for purification. The column was washed with TE buffer until optical density at 280 nm was dropped to under 0.01 and eluted the recombinant proteins with 5 mM desthio-biotin containing TE buffer.

Qualitative and Quantitative Analyses of Purified Phytochromes

Protein samples were analyzed by SDS-PAGE using 10% polyacrylamide minigels and were stained with 0.25% Coomassie Brilliant Blue R250. For Western blot analysis, the protein bands on the SDS-PAGE gel were transferred to a PVDF membrane (Hybond-P, Amersham-Pharmacia), and the membrane was incubated with oat phytochrome A-specific monoclonal antibodies, oat-22 and oat-25 (Cordonnier, 1989), for 2 hours, and developed by using an ECL™ western blotting analysis system (Amersham). To investigate whether the chromophore ligated with phytochrome proteins, Zinc blot analysis was carried out as described (Berkelman and Lagarias, 1986). The protein samples were separated on a SDS-PAGE gel and soaked in 20 mM zinc acetate/150 mM Tris-HCl, pH 7.0 for 5-30 min at room temperature with gentle agitation. The chromophores covalently linked phytochrome was visualized under UV light (312 nm) as a bright pink colored band. The concentrations of protein samples were determined by Bradford method using bovine serum albumin (BSA) as a standard.

Photochemical Analyses of Recombinant Phytochromes

All experiments were performed under safety green light conditions with a maximal transmittance at 500 nm through a specific filter (Rosco). The absorption spectra of holo-phytochromes were recorded in the range between 260 and 800 nm by a diode array UV/VIS spectrophotometer (Varian, Cary3 Bio EL97063574). The absorption spectra of the Pr and Pfr forms of each mutant phytochrome were measured after red or far-red light irradiation. A fiber optic illuminator system (Cole-Palmer) equipped with 656 and 730 nm interference filters (Oriel) was used as a light source. The light intensity was 8 W/$m^2$ for red light and 6 W/$m^2$ for far-red light. Red or far-red lights were illuminated to each sample for at least 2 min. A difference spectrum was calculated by subtracting the Pr spectrum from the Pfr spectrum, or reverse subtraction. From the absorption and difference spectra, the absorption maxima of Pr and Pfr ($\lambda_{pr}$ and $\lambda_{pfr}$) were determined. To investigate non-photochemical reversion of Pfr to Pr (dark reversion), phytochromes were irradiated with red light to transform Pfr. The amounts of [Pfr] and [Ptot] were then checked in a time-dependant manner with UV/VIS spectrophotometer at room temperature (Varian, Cary3 Bio EL97063574).

Construction of Plant Expression Vectors

Oat phyA gene and wavelength-shifted mutant genes were subcloned into pCambia 1200 binary plasmid containing a hygromycin selective marker. For expression of phytochromes, CaMV (Cauliflower mosaic virus) 35S promoter and NOS terminator originated from the nopaline synthase gene of *Agrobacterium* were used in all plant expression constructs. The fragment of oat phyA gene was prepared with sequential enzymatic treatment: EcoRI digestion, T4 polymerase treatment for making blunt end at 3' end prior to BamHI digestion for 5' end. This fragment was ligated with the digested vector using the BamHI and EcoICRI. The pCambia1200 containing oat phyA gene was then used for subcloning of the wavelength-shifted mutant phytochromes. As exchanging each fragment from KpnI to AvrII between the wild type and wavelength-shifted mutants, the mutated phytochrome genes were easily subcloned into plant expression vector.

Plant Growth Conditions and Transformation

Arabidopsis thaliana ecotype Col-0 and phyA mutant allele, phyA-211 provided from Arabidopsis Biological Research Center at Ohio (ABRC), were used in all experiments (Reed et al, 1994). The plant expression vectors containing each wavelength-shifted mutant and wild type were transformed into *Agrobacterium tumefaciens* GV3101. With each transformed *Agrobacterium*, *Arabidopsis* transformation was followed by *Agrobacterium*-mediated floral dip method (Clough and Bent, 1998). For the transformation, *Arabidopsis* plants were grown to flowering stage at 22-24° C. at long day condition. The transformed *Agrobacterium* was grown at 28° C. in sterilized YEP (10 g tryptone, 10 g yeast extract, 5 g NaCl per liter of water) including 50 μg/mL of hygromycin. The cultured transformants were harvested and resuspended in infiltration medium to approximately 0.8 of a final $OD_{600}$ prior to use. Infiltration medium is composed of ½ strength MS basal medium, 5.0% sucrose, 0.44 μM benzylamino purine, 0.005% Silwet L-77 and B5 vitamins. After the transformation by floral dip method, the plants were cultured under cool white light at 22-24° C.

Selection and Analyses of Transgenic Plants

After transformation, seeds (heterozygous T1 line) were harvested and surface sterilized as follows: treated with 95% ethanol for 30-60 sec, then with 10% (v/v) commercial bleach containing 0.05% Tween-20 for 5 min, followed by three times rinses with sterile water. The washed seeds were stored at cold and dark room for 3~5 days to synchronize the germination. To obtain transgenic plants of homozygous wild type (wt-OX) and each wavelength-shifted mutants, the sterilized seeds were sown on hygromycin-selection plates containing 0.5×MS medium, 0.8% phytoagar and 50 μg/mL of hygromycin. Transgenic plants were identified as antibiotics-resistant seedlings that produced green leaves and well-established roots on the selective medium. The grown plants on the selective media were allowed to self-pollinate by transplanting into heavily moistened potting soil. The harvested seeds (heterozygous T2 line) from the first screening were tested again to obtain 3:1 segregated plants, which contain single allele of T-DNA in their chromosomes. To obtain homozygous T3 line, the grown young plants tested from 3:1 segregation on plates containing antibiotics were transferred to moistened soil. Then, the seeds from each transformed plant (T3 seeds) were sown on plats containing antibiotics and selected as homozygous line when all of the sown seeds were grown up to show antibiotics resistance. The screened homozygous transgenic lines were confirmed by Western blot, RT-PCR (Reverse Transcription-Polymerase Chain Reaction), and genomic southern blot analysis. All physiological experiments were performed with the T3 seeds.

Light Sources and Spectral Measurements

Plants were illuminated with fluorescent cool white light for the growth. Monochromic far-red light (photon irradiance approximately 700~800 nm, peak of maximum 738 nm) was provided from a light emitting diode (LED) array at LED incubator (VS-9108M-LED, Vision Scientific Co. Seoul, Korea). The used photon fluence rate was measured by radiometer IL-1700 (International Light, Newburyport, Mass.) with detector SED033 (#7963, International Light).

Physiological Analyses

To synchronize seed germination, sterilized seeds were kept in the dark at 4° C. for 3~5 days, then exposed under white light for 1~2 hrs, and kept in the dark for 1 day prior to the treatment for a specific light conditions in experiments (Fankhauser and Casal, 2004).

To test shade sensitivity of the transgenic plants, wild-type and mutant phyA transgenic seedlings were grown in long-day cycles (LD, 16-h light/8-h dark cycle) for 3 days (white light, 60 μmole/m²·s) followed grown in short-day cycles (SD, 8-h light/16-h dark cycle) for 3 days without or with a 15 min end-of-day far-red light treatment which mimics the shade condition (FR, 10 μmole/m²·s) (Devlin et al., 1999). Also, to investigate the shade tolerance from adult plants, they were cultured under LD condition for 2 weeks prior to transferring to LED growth chamber to each different light condition (LD+FR1, W:FR=60 μmole/m²·s:5 μmole/m²·s; LD+FR2, W:FR=60 μmole/m²·s: 10 μmole/m²·s). Then, they were cultured for 3 weeks under different light conditions. The largest leaf from each transgenic plant was measured to investigate leaf areas and petioles length. The pictures of transgenic seedlings or plants were taken and the hypocotyls lengths, petiole lengths, leaf-lengths and leaf-widths were measured by using NIH image analyzer program.

To investigate the effect of wavelength-shifted phytochromes on the recognition of proximity, 6 plants or 40 plants of each transgenic plant were planted in a pot with 10 cm diameter. To synchronize the developmental stage in the same pot, 2 week-grown young plants at the same stage were transferred to new pots.

All the experiments were performed with each two different homozygous plants containing each wavelength-shifted phytochrome genes. All experiments were repeated at least three times.

REFERENCES

Ballare, C. L. (1999) Keeping up with the neighbours: phytochrome sensing and other signaling mechanisms. *Trends Plant Sci.* 4, 97-102.

Berkelman, T. R., and Lagarias, J. C. (1986) Visualization of bilin-linked peptides and proteins in polyacrylamide gels. *Anal. Biochem.* 156, 194-201.

Boccalandro, H. E., Ploschuk, E. L., Yanovski, M. J., Sanchez, R. A., Gatz, C., and Casal, J. J. (2003) Increased phytochrome B alleviates density effects on tuber yield of field potato crops. *Plat Physiol.* 133, 1539-1546.

Botto, J. F., Ahn, J. H., and Weigel, D. (1996) Phytochrome A mediates the promotion of germination by very low fluences of light and canopy shade light in *Arabidopsis*. *Plant Physiol.* 110, 439-444.

Boylan, M. T., and Quail, P. H. (1989) Oat phytochrome is biologically active in transgenic tomatoes. *Plant Cell* 1, 765-773.

Cérdan, P. D., and Chory, J. (2003) Regulation of flowering time by light quality. *Nature* 423, 3102-3106.

Chen, M., Chory, J., and Fankhauser, C. (2004) Light signal transduction in higher plants. *Annu. Rev. Genet.* 38, 87-117.

Clough, S. J., and Bent, A. F. (1998) Floral dip: a simplified method for *Agrobacterium*-mediated transformation of *Arabidopsis thaliana. Plant J.* 16, 735-43.

Cordonnier, M.-M (1989) Monoclonal antibodies: Molecular probes for the study of phytochrome. *Photochem. Photobiol.* 49, 821-831.

Devlin, P. F., Yanovski, M. J., and Kay, S. A. (2003) A genomic Analysis of the shade avoidance response in *Arabidopsis*. *Plant Physiol.* 133, 1617-1629.

Gilbert, I. R., Jarvis, P. G., and Smith, H. (2001) Proximity signal and shade avoidance differences between early and late successional trees. *Nature* 411, 792-795.

Hayama, R., and Coupland, G. (2003) Shedding light on the circadian clock and the photoperiodic control of flowering. *Curr. Opin. Plant Biol.* 6, 13-19.

Heyer, A. G., Mozley, D., Landschutze, V., Thomas B., and Gatz, C. (1995) Function of phytochrome A in potato plants as revealed through the study of transgenic plants. *Plant Physiol.* 109, 53-61.

Johnson, E., Bradley, M., Harberd, N. P., and Whitelam, G. C. (1994) Photoresponses of light-grown phyA mutants of *Arabidopsis*. *Plant Physiol.* 105, 141-149.

Kim, J-I., Kozhukh, G. V., and Song, P-S. (2002) Phytochrome-mediated signal transduction pathways in plants. *Biochem. Biophys. Res. Comm.* 298, 457-463.

Kim, J.-I., Shen, Y., Han, Y.-J., Park, J.-E., Kirchenbauer, D., Soh, M.-S., Nagy, F., Schafer, E., and Song, P.-S. (2004) Phytochrome phosphorylation modulates light signaling by influencing the protein-protein interaction. *Plant Cell* 16, 2629-2640.

Mockler, T., Yang, H., Yu, X., Parikh, D., Cheng, Y., Dolan, S., and Chen, L. (2003) Regulation of photoperiodic flowering by *Arabidopsis* photoreceptors. *Proc. Natl. Acad. Sci. USA* 100, 2140-2145.

Morelli, G., and Ruberti, I. (2000) Shade avoidance responses. Driving Auxin along lateral routes. *Plant Physiol.* 122, 621-626.

Neff, M. N., Fankhauser, C., and Chory, J. (2000) Light: an indicator of time and place. *Genes & Dev.* 14, 257-271.

Reed, J. W., Nagatani, A., Elich, T. D., Fagan, M., and Chory, J. (1994) Phytochrome A and phytochrome B have overlapping but distinct function in *Arabidopsis* development. *Plant Physiol.* 104, 1139-1149.

Robson, P. R. H., Whitelam, G. C., and Smith, H. (1993) Selected components of the shade-avoidance syndrome are displayed in a normal manner in mutants of *Arabidopsis thaliana* and *Brassica rapa* deficient in phytochrome B. *Plany Physiol.* 102, 1179-1184.

Robson, P. R. H., McCormac, A. C., Irvine, A. S., and Smith, H. (1996) Genetic engineering of harvest index in tobacco through overexpression of a phytochrome gene. *Nature Biotech.* 14, 995-998.

Robson, P. R. H., and Smith, H. (1997) Fundamental and biotechnological applications of phytochrome transgenes. *Plant Cell Environ.* 20, 831-839.

Shlumukov, L. R., Barro, F., Barcelo, P., Lazzeri, P., and Smith, H. (2001) Establishment of far-red high irradiance responses in wheat through transgenic expression of an oat phytochrome A gene. *Plant Cell Environ.* 24, 703-712.

Sineshchekov, V., Koppel, L., Shlumukov, L., Barro, F., Barcelo, P., Lazzeri, P., and Smith, H. (2001) Fluorescence and photochemical properties of phytochromes in wild-type wheat and transgenic line overexpressing an oat phytochrome A (PHYA) gene: functional implications. *Plant Cell Environ.* 24, 1289-1297.

Smith, H., and Whitelam, G. C. (1997), The shade avoidance syndrome: multiple responses mediated by multiple phytochromes. *Plant Cell Environ.* 20, 840-844.

Smith, H. (2000) Phytochromes and light signal perception by plants-an emerging synthesis. *Nature* 407, 585-591.

Sullivan, J. A., and Deng, X. W. (2003) From seed to seed; the role of photoreceptors in *Arabidopsis* development. *Dev. Biol.* 260, 289-297.

---

What is claimed is:

1. An isolated nucleic acid molecule encoding the modified phytochrome A (PHYA) comprising the amino acid sequence given in SEQ ID NO: 1 whose Pr absorption spectra are shifted to longer wavelength to confer shade tolerance in vivo.

2. An expression vector for transformation of plant cells comprising:

(a) a polynucleotide of SEQ ID NO: 1 encoding a modified phytochrome A; and (b) regulatory sequences operatively linked to the polynucleotide such that the polynucleotide is expressable in the plant cell, wherein said expression results in spectrally red-shifted phytochrome that are effective in detecting far-red light in the shade.

3. A transgenic plant cell transformed with the expression vector of claim 2.

4. A transgenic plant having shade tolerance grown from the transgenic plant cell of claim 3.

* * * * *

SEQUENCE LISTING

<160> NUMBER OF SEQ ID NOS: 38

<210> SEQ ID NO 1
<211> LENGTH: 1129
<212> TYPE: PRT
<213> ORGANISM: Avena sp.

<400> SEQUENCE: 1

```
Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
        35                  40                  45

Val Glu Ala Gln Arg Asp Gly Pro Pro Val Gln Gln Gly Arg Ser Glu
    50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
                100                 105                 110
```

-continued

```
Val Pro Ser Val Asp Asp Pro Arg Leu Gly Ile Gly Thr Asn Val
        115                 120                 125

Arg Ser Leu Phe Ser Asp Gln Gly Ala Thr Ala Leu His Lys Ala Leu
    130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
                180                 185                 190

Ala Ala Gly Ala Leu Gln Ser Tyr Lys Leu Ala Ala Lys Ala Ile Ser
        195                 200                 205

Lys Ile Gln Ser Leu Pro Gly Gly Ser Met Glu Met Leu Cys Asn Thr
    210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
                260                 265                 270

Ile Pro Gln Ala Ala Arg Phe Leu Phe Met Lys Asn Lys Val Arg Met
        275                 280                 285

Ile Cys Asp Cys Arg Ala Arg Ser Ile Lys Val Ile Glu Ala Glu Ala
    290                 295                 300

Leu Pro Phe Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
                325                 330                 335

Val Met Ala Val Val Val Asn Glu Asn Glu Glu Asp Glu Ala Glu
                340                 345                 350

Ser Glu Gln Pro Ala Gln Gln Lys Lys Lys Leu Trp Gly Leu
        355                 360                 365

Leu Val Cys His His Glu Ser Pro Arg Tyr Val Pro Phe Pro Leu Arg
    370                 375                 380

Ala Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
                420                 425                 430

Ile Val Ser Gly Asn Pro Asn Ile Met Asp Leu Val Lys Cys Asp Gly
        435                 440                 445

Ala Ala Leu Leu Tyr Gly Gly Lys Val Trp Arg Leu Arg Asn Ala Pro
    450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
                500                 505                 510

Lys Ile Asn Ser Lys Asp Ile Leu Phe Trp Phe Arg Ser His Thr Ala
        515                 520                 525

Ala Glu Ile Arg Trp Gly Gly Ala Lys Asn Asp Pro Ser Asp Met Asp
```

-continued

```
                530                 535                 540
Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
                565                 570                 575

Ile His Ser Leu Gln Leu Ile Leu Arg Gly Thr Leu Asn Asp Ala Ser
                580                 585                 590

Lys Pro Lys Arg Glu Ala Ser Leu Asp Asn Gln Ile Gly Asp Leu Lys
                595                 600                 605

Leu Asp Gly Leu Ala Glu Leu Gln Ala Val Thr Ser Glu Met Val Arg
610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
                660                 665                 670

Ser Val Pro Val Val Gln Arg Met Leu Tyr Leu Ala Leu Gln Gly Lys
                675                 680                 685

Glu Glu Lys Glu Val Arg Phe Glu Val Lys Thr His Gly Pro Lys Arg
                690                 695                 700

Asp Asp Gly Pro Val Ile Leu Val Val Asn Ala Cys Ala Ser Arg Asp
705                 710                 715                 720

Leu His Asp His Val Val Gly Val Cys Phe Val Ala Gln Asp Met Thr
                725                 730                 735

Val His Lys Leu Val Met Asp Lys Phe Thr Arg Val Glu Gly Asp Tyr
                740                 745                 750

Lys Ala Ile Ile His Asn Pro Asn Pro Leu Ile Pro Pro Ile Phe Gly
                755                 760                 765

Ala Asp Glu Phe Gly Trp Cys Ser Glu Trp Asn Ala Ala Met Thr Lys
                770                 775                 780

Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
                805                 810                 815

Ala Phe Val Ser Leu Cys Val Leu Ile Asn Ser Ala Leu Ala Gly Glu
                820                 825                 830

Glu Thr Glu Lys Ala Pro Phe Gly Phe Phe Asp Arg Ser Gly Lys Tyr
                835                 840                 845

Ile Glu Cys Leu Leu Ser Ala Asn Arg Lys Glu Asn Glu Gly Gly Leu
850                 855                 860

Ile Thr Gly Val Phe Cys Phe Ile His Val Ala Ser His Glu Leu Gln
865                 870                 875                 880

His Ala Leu Gln Val Gln Ala Ser Glu Gln Thr Ser Leu Lys Arg
                885                 890                 895

Leu Lys Ala Phe Ser Tyr Met Arg His Ala Ile Asn Asn Pro Leu Ser
                900                 905                 910

Gly Met Leu Tyr Ser Arg Lys Ala Leu Lys Asn Thr Asp Leu Asn Glu
                915                 920                 925

Glu Gln Met Lys Gln Ile His Val Gly Asp Asn Cys His His Gln Ile
                930                 935                 940

Asn Lys Ile Leu Ala Asp Leu Asp Gln Asp Ser Ile Thr Glu Lys Ser
945                 950                 955                 960
```

```
Ser Cys Leu Asp Leu Glu Met Ala Glu Phe Leu Leu Gln Asp Val Val
            965                 970                 975
Val Ala Ala Val Ser Gln Val Leu Ile Thr Cys Gln Gly Lys Gly Ile
            980                 985                 990
Arg Ile Ser Cys Asn Leu Pro Glu Arg Phe Met Lys Gln Ser Val Tyr
            995                1000                1005
Gly Asp Gly Val Arg Leu Gln Gln Ile Leu Ser Asp Phe Leu Phe
        1010                1015                1020
Ile Ser Val Lys Phe Ser Pro Val Gly Gly Ser Val Glu Ile Ser
        1025                1030                1035
Ser Lys Leu Thr Lys Asn Ser Ile Gly Glu Asn Leu His Leu Ile
        1040                1045                1050
Asp Leu Glu Leu Arg Ile Lys His Gln Gly Leu Gly Val Pro Ala
        1055                1060                1065
Glu Leu Met Ala Gln Met Phe Glu Glu Asp Asn Lys Glu Gln Ser
        1070                1075                1080
Glu Glu Gly Leu Ser Leu Leu Val Ser Arg Asn Leu Leu Arg Leu
        1085                1090                1095
Met Asn Gly Asp Val Arg His Leu Arg Glu Ala Gly Val Ser Thr
        1100                1105                1110
Phe Ile Ile Thr Ala Glu Leu Ala Ser Ala Pro Thr Ala Met Gly
        1115                1120                1125
Gln

<210> SEQ ID NO 2
<211> LENGTH: 1129
<212> TYPE: PRT
<213> ORGANISM: Avena sp.

<400> SEQUENCE: 2

Met Ser Ser Ser Arg Pro Ala Ser Ser Ser Ser Arg Asn Arg Gln
1               5                  10                  15
Ser Ser Gln Ala Arg Val Leu Ala Gln Thr Thr Leu Asp Ala Glu Leu
            20                  25                  30
Asn Ala Glu Tyr Glu Glu Ser Gly Asp Ser Phe Asp Tyr Ser Lys Leu
            35                  40                  45
Val Glu Ala Gln Arg Asp Gly Pro Pro Val Gln Gln Gly Arg Ser Glu
    50                  55                  60
Lys Val Ile Ala Tyr Leu Gln His Ile Gln Lys Gly Lys Leu Ile Gln
65                  70                  75                  80
Thr Phe Gly Cys Leu Leu Ala Leu Asp Glu Lys Ser Phe Asn Val Ile
                85                  90                  95
Ala Phe Ser Glu Asn Ala Pro Glu Met Leu Thr Thr Val Ser His Ala
            100                 105                 110
Val Pro Ser Val Asp Asp Pro Arg Leu Gly Ile Gly Thr Asn Val
            115                 120                 125
Arg Ser Leu Phe Ser Asp Gln Gly Ala Thr Ala Leu His Lys Ala Leu
    130                 135                 140
Gly Phe Ala Asp Val Ser Leu Leu Asn Pro Ile Leu Val Gln Cys Lys
145                 150                 155                 160
Thr Ser Gly Lys Pro Phe Tyr Ala Ile Val His Arg Ala Thr Gly Cys
                165                 170                 175
Leu Val Val Asp Phe Glu Pro Val Lys Pro Thr Glu Phe Pro Ala Thr
            180                 185                 190
```

-continued

```
Ala Ala Gly Ala Leu Gln Ser Tyr Lys Leu Ala Ala Lys Ala Ile Ser
        195                 200                 205
Lys Ile Gln Ser Leu Pro Gly Gly Ser Met Glu Met Leu Cys Asn Thr
210                 215                 220
Val Val Lys Glu Val Phe Asp Leu Thr Gly Tyr Asp Arg Val Met Ala
225                 230                 235                 240
Tyr Lys Phe His Glu Asp His Gly Glu Val Phe Ser Glu Ile Thr
                245                 250                 255
Lys Pro Gly Leu Glu Pro Tyr Leu Gly Leu His Tyr Pro Ala Thr Asp
                260                 265                 270
Ile Pro Gln Ala Ala Arg Phe Leu Phe Met Lys Asn Lys Val Arg Met
            275                 280                 285
Ile Cys Asp Cys Arg Ala Arg Ser Ile Lys Val Ile Glu Ala Glu Ala
        290                 295                 300
Leu Pro Phe Asp Ile Ser Leu Cys Gly Ser Ala Leu Arg Ala Pro His
305                 310                 315                 320
Ser Cys His Leu Gln Tyr Met Glu Asn Met Asn Ser Ile Ala Ser Leu
                325                 330                 335
Val Met Ala Val Val Asn Glu Asn Glu Asp Asp Glu Ala Glu
                340                 345                 350
Ser Glu Gln Pro Ala Gln Gln Lys Lys Lys Leu Trp Gly Leu
            355                 360                 365
Leu Val Cys His His Glu Ser Pro Arg Tyr Val Pro Phe Pro Leu Arg
        370                 375                 380
Phe Ala Cys Glu Phe Leu Ala Gln Val Phe Ala Val His Val Asn Arg
385                 390                 395                 400
Glu Phe Glu Leu Glu Lys Gln Leu Arg Glu Lys Asn Ile Leu Lys Met
                405                 410                 415
Gln Thr Met Leu Ser Asp Met Leu Phe Arg Glu Ala Ser Pro Leu Thr
            420                 425                 430
Ile Val Ser Gly Asn Pro Asn Ile Met Asp Leu Val Lys Cys Asp Gly
        435                 440                 445
Ala Ala Leu Leu Tyr Gly Gly Lys Val Trp Arg Leu Arg Asn Ala Pro
450                 455                 460
Thr Glu Ser Gln Ile His Asp Ile Ala Phe Trp Leu Ser Asp Val His
465                 470                 475                 480
Arg Asp Ser Thr Gly Leu Ser Thr Asp Ser Leu His Asp Ala Gly Tyr
                485                 490                 495
Pro Gly Ala Ala Ala Leu Gly Asp Met Ile Cys Gly Met Ala Val Ala
            500                 505                 510
Lys Ile Asn Ser Lys Asp Ile Leu Phe Trp Phe Arg Ser His Thr Ala
        515                 520                 525
Ala Glu Ile Arg Trp Gly Gly Ala Lys Asn Asp Pro Ser Asp Met Asp
            530                 535                 540
Asp Ser Arg Arg Met His Pro Arg Leu Ser Phe Lys Ala Phe Leu Glu
545                 550                 555                 560
Val Val Lys Met Lys Ser Leu Pro Trp Ser Asp Tyr Glu Met Asp Ala
                565                 570                 575
Ile His Ser Leu Gln Leu Ile Leu Arg Gly Thr Leu Asn Asp Ala Ser
            580                 585                 590
Lys Pro Lys Arg Glu Ala Ser Leu Asp Asn Gln Ile Gly Asp Leu Lys
        595                 600                 605
```

-continued

```
Leu Asp Gly Leu Ala Glu Leu Gln Ala Val Thr Ser Glu Met Val Arg
    610                 615                 620
Leu Met Glu Thr Ala Thr Val Pro Ile Leu Ala Val Asp Gly Asn Gly
625                 630                 635                 640
Leu Val Asn Gly Trp Asn Gln Lys Ala Ala Glu Leu Thr Gly Leu Arg
                645                 650                 655
Val Asp Asp Ala Ile Gly Arg His Ile Leu Thr Leu Val Glu Asp Ser
                660                 665                 670
Ser Val Pro Val Val Gln Arg Met Leu Tyr Leu Ala Leu Gln Gly Lys
            675                 680                 685
Glu Glu Lys Glu Val Arg Phe Glu Val Lys Thr His Gly Pro Lys Arg
    690                 695                 700
Asp Asp Gly Pro Val Ile Leu Val Val Asn Ala Cys Ala Ser Arg Asp
705                 710                 715                 720
Leu His Asp His Val Val Gly Val Cys Phe Val Ala Gln Asp Met Thr
                725                 730                 735
Val His Lys Leu Val Met Asp Lys Phe Thr Arg Val Glu Gly Asp Tyr
                740                 745                 750
Lys Ala Ile Ile His Asn Pro Asn Pro Leu Ile Pro Pro Ile Phe Gly
            755                 760                 765
Ala Asp Glu Phe Gly Trp Cys Ser Glu Trp Asn Ala Ala Met Thr Lys
    770                 775                 780
Leu Thr Gly Trp Asn Arg Asp Glu Val Leu Asp Lys Met Leu Leu Gly
785                 790                 795                 800
Glu Val Phe Asp Ser Ser Asn Ala Ser Cys Pro Leu Lys Asn Arg Asp
                805                 810                 815
Ala Phe Val Ser Leu Cys Val Leu Ile Asn Ser Ala Leu Ala Gly Glu
                820                 825                 830
Glu Thr Glu Lys Ala Pro Phe Gly Phe Phe Asp Arg Ser Gly Lys Tyr
            835                 840                 845
Ile Glu Cys Leu Leu Ser Ala Asn Arg Lys Glu Asn Glu Gly Gly Leu
    850                 855                 860
Ile Thr Gly Val Phe Cys Phe Ile His Val Ala Ser His Glu Leu Gln
865                 870                 875                 880
His Ala Leu Gln Val Gln Gln Ala Ser Glu Gln Thr Ser Leu Lys Arg
                885                 890                 895
Leu Lys Ala Phe Ser Tyr Met Arg His Ala Ile Asn Asn Pro Leu Ser
            900                 905                 910
Gly Met Leu Tyr Ser Arg Lys Ala Leu Lys Asn Thr Asp Leu Asn Glu
    915                 920                 925
Glu Gln Met Lys Gln Ile His Val Gly Asp Asn Cys His His Gln Ile
    930                 935                 940
Asn Lys Ile Leu Ala Asp Leu Asp Gln Asp Ser Ile Thr Glu Lys Ser
945                 950                 955                 960
Ser Cys Leu Asp Leu Glu Met Ala Glu Phe Leu Leu Gln Asp Val Val
                965                 970                 975
Val Ala Ala Val Ser Gln Val Leu Ile Thr Cys Gln Gly Lys Gly Ile
                980                 985                 990
Arg Ile Ser Cys Asn Leu Pro Glu Arg Phe Met Lys Gln Ser Val Tyr
            995                 1000                1005
Gly Asp Gly Val Arg Leu Gln Gln Ile Leu Ser Asp Phe Leu Phe
    1010                1015                1020
Ile Ser Val Lys Phe Ser Pro Val Gly Gly Ser Val Glu Ile Ser
```

```
      1025                1030                1035
Ser Lys Leu Thr Lys Asn Ser Ile Gly Glu Asn Leu His Leu Ile
    1040                1045                1050

Asp Leu Glu Leu Arg Ile Lys His Gln Gly Leu Gly Val Pro Ala
    1055                1060                1065

Glu Leu Met Ala Gln Met Phe Glu Glu Asp Asn Lys Glu Gln Ser
    1070                1075                1080

Glu Glu Gly Leu Ser Leu Leu Val Ser Arg Asn Leu Leu Arg Leu
    1085                1090                1095

Met Asn Gly Asp Val Arg His Leu Arg Glu Ala Gly Val Ser Thr
    1100                1105                1110

Phe Ile Ile Thr Ala Glu Leu Ala Ser Ala Pro Thr Ala Met Gly
    1115                1120                1125

Gln

<210> SEQ ID NO 3
<211> LENGTH: 1129
<212> TYPE: PRT
<213> ORGANISM: Avena sp.

<400> SEQUENCE: 3

Met Ser Ser Ser Arg Pro Ala Ser Ser Ser Ser Arg Asn Arg Gln
1               5                  10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
            35                  40                  45

Val Glu Ala Gln Arg Asp Gly Pro Pro Val Gln Gln Gly Arg Ser Glu
50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
                100                 105                 110

Val Pro Ser Val Asp Asp Pro Arg Leu Gly Ile Gly Thr Asn Val
            115                 120                 125

Arg Ser Leu Phe Ser Asp Gln Gly Ala Thr Ala Leu His Lys Ala Leu
130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
                180                 185                 190

Ala Ala Gly Ala Leu Gln Ser Tyr Lys Leu Ala Ala Lys Ala Ile Ser
            195                 200                 205

Lys Ile Gln Ser Leu Pro Gly Gly Ser Met Glu Met Leu Cys Asn Thr
210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
```

```
                       260                 265                 270
Ile Pro Gln Ala Ala Arg Phe Leu Phe Met Lys Asn Lys Val Arg Met
            275                 280                 285
Ile Cys Asp Cys Arg Ala Arg Ser Ile Lys Val Ile Glu Ala Glu Ala
            290                 295                 300
Leu Pro Phe Asp Ile Ser Leu Cys Gly Ser Ala Leu Arg Ala Pro His
305                 310                 315                 320
Ser Cys His Leu Gln Tyr Met Glu Asn Met Asn Ser Ile Ala Ser Leu
            325                 330                 335
Val Met Ala Val Val Asn Glu Asn Glu Glu Asp Glu Ala Glu
            340                 345                 350
Ser Glu Gln Pro Ala Gln Gln Lys Lys Lys Leu Trp Gly Leu
            355                 360                 365
Leu Val Cys His His Glu Ser Pro Arg Tyr Val Pro Phe Pro Leu Arg
            370                 375                 380
Val Ala Cys Glu Phe Leu Ala Gln Val Phe Ala Val His Val Asn Arg
385                 390                 395                 400
Glu Phe Glu Leu Glu Lys Gln Leu Arg Glu Lys Asn Ile Leu Lys Met
            405                 410                 415
Gln Thr Met Leu Ser Asp Met Leu Phe Arg Glu Ala Ser Pro Leu Thr
            420                 425                 430
Ile Val Ser Gly Asn Pro Asn Ile Met Asp Leu Val Lys Cys Asp Gly
            435                 440                 445
Ala Ala Leu Leu Tyr Gly Gly Lys Val Trp Arg Leu Arg Asn Ala Pro
            450                 455                 460
Thr Glu Ser Gln Ile His Asp Ile Ala Phe Trp Leu Ser Asp Val His
465                 470                 475                 480
Arg Asp Ser Thr Gly Leu Ser Thr Asp Ser Leu His Asp Ala Gly Tyr
            485                 490                 495
Pro Gly Ala Ala Ala Leu Gly Asp Met Ile Cys Gly Met Ala Val Ala
            500                 505                 510
Lys Ile Asn Ser Lys Asp Ile Leu Phe Trp Phe Arg Ser His Thr Ala
            515                 520                 525
Ala Glu Ile Arg Trp Gly Gly Ala Lys Asn Asp Pro Ser Asp Met Asp
            530                 535                 540
Asp Ser Arg Arg Met His Pro Arg Leu Ser Phe Lys Ala Phe Leu Glu
545                 550                 555                 560
Val Val Lys Met Lys Ser Leu Pro Trp Ser Asp Tyr Glu Met Asp Ala
            565                 570                 575
Ile His Ser Leu Gln Leu Ile Leu Arg Gly Thr Leu Asn Asp Ala Ser
            580                 585                 590
Lys Pro Lys Arg Glu Ala Ser Leu Asp Asn Gln Ile Gly Asp Leu Lys
            595                 600                 605
Leu Asp Gly Leu Ala Glu Leu Gln Ala Val Thr Ser Glu Met Val Arg
            610                 615                 620
Leu Met Glu Thr Ala Thr Val Pro Ile Leu Ala Val Asp Gly Asn Gly
625                 630                 635                 640
Leu Val Asn Gly Trp Asn Gln Lys Ala Ala Glu Leu Thr Gly Leu Arg
            645                 650                 655
Val Asp Asp Ala Ile Gly Arg His Ile Leu Thr Leu Val Glu Asp Ser
            660                 665                 670
Ser Val Pro Val Val Gln Arg Met Leu Tyr Leu Ala Leu Gln Gly Lys
            675                 680                 685
```

```
Glu Glu Lys Glu Val Arg Phe Glu Val Lys Thr His Gly Pro Lys Arg
    690             695             700
Asp Asp Gly Pro Val Ile Leu Val Val Asn Ala Cys Ala Ser Arg Asp
705             710             715             720
Leu His Asp His Val Gly Val Cys Phe Val Ala Gln Asp Met Thr
            725             730             735
Val His Lys Leu Val Met Asp Lys Phe Thr Arg Val Glu Gly Asp Tyr
        740             745             750
Lys Ala Ile Ile His Asn Pro Asn Pro Leu Ile Pro Pro Ile Phe Gly
        755             760             765
Ala Asp Glu Phe Gly Trp Cys Ser Glu Trp Asn Ala Ala Met Thr Lys
770             775             780
Leu Thr Gly Trp Asn Arg Asp Glu Val Leu Asp Lys Met Leu Leu Gly
785             790             795             800
Glu Val Phe Asp Ser Ser Asn Ala Ser Cys Pro Leu Lys Asn Arg Asp
            805             810             815
Ala Phe Val Ser Leu Cys Val Leu Ile Asn Ser Ala Leu Ala Gly Glu
            820             825             830
Glu Thr Glu Lys Ala Pro Phe Gly Phe Phe Asp Arg Ser Gly Lys Tyr
        835             840             845
Ile Glu Cys Leu Leu Ser Ala Asn Arg Lys Glu Asn Glu Gly Gly Leu
    850             855             860
Ile Thr Gly Val Phe Cys Phe Ile His Val Ala Ser His Glu Leu Gln
865             870             875             880
His Ala Leu Gln Val Gln Gln Ala Ser Glu Gln Thr Ser Leu Lys Arg
            885             890             895
Leu Lys Ala Phe Ser Tyr Met Arg His Ala Ile Asn Asn Pro Leu Ser
            900             905             910
Gly Met Leu Tyr Ser Arg Lys Ala Leu Lys Asn Thr Asp Leu Asn Glu
        915             920             925
Glu Gln Met Lys Gln Ile His Val Gly Asp Asn Cys His His Gln Ile
    930             935             940
Asn Lys Ile Leu Ala Asp Leu Asp Gln Asp Ser Ile Thr Glu Lys Ser
945             950             955             960
Ser Cys Leu Asp Leu Glu Met Ala Glu Phe Leu Leu Gln Asp Val Val
            965             970             975
Val Ala Ala Val Ser Gln Val Leu Ile Thr Cys Gln Gly Lys Gly Ile
        980             985             990
Arg Ile Ser Cys Asn Leu Pro Glu Arg Phe Met Lys Gln Ser Val Tyr
    995             1000            1005
Gly Asp Gly Val Arg Leu Gln Gln Ile Leu Ser Asp Phe Leu Phe
    1010            1015            1020
Ile Ser Val Lys Phe Ser Pro Val Gly Gly Ser Val Glu Ile Ser
    1025            1030            1035
Ser Lys Leu Thr Lys Asn Ser Ile Gly Glu Asn Leu His Leu Ile
    1040            1045            1050
Asp Leu Glu Leu Arg Ile Lys His Gln Gly Leu Gly Val Pro Ala
    1055            1060            1065
Glu Leu Met Ala Gln Met Phe Glu Glu Asp Asn Lys Glu Gln Ser
    1070            1075            1080
Glu Glu Gly Leu Ser Leu Leu Val Ser Arg Asn Leu Leu Arg Leu
    1085            1090            1095
```

```
Met Asn Gly Asp Val Arg His Leu Arg Glu Ala Gly Val Ser Thr
    1100            1105                1110
Phe Ile Ile Thr Ala Glu Leu Ala Ser Ala Pro Thr Ala Met Gly
1115            1120                1125
Gln

<210> SEQ ID NO 4
<211> LENGTH: 1129
<212> TYPE: PRT
<213> ORGANISM: Avena sp.

<400> SEQUENCE: 4

Met Ser Ser Ser Arg Pro Ala Ser Ser Ser Ser Arg Asn Arg Gln
1               5                   10                  15
Ser Ser Gln Ala Arg Val Leu Ala Gln Thr Thr Leu Asp Ala Glu Leu
                20                  25                  30
Asn Ala Glu Tyr Glu Glu Ser Gly Asp Ser Phe Asp Tyr Ser Lys Leu
            35                  40                  45
Val Glu Ala Gln Arg Asp Gly Pro Pro Val Gln Gln Gly Arg Ser Glu
50                  55                  60
Lys Val Ile Ala Tyr Leu Gln His Ile Gln Lys Gly Lys Leu Ile Gln
65              70                  75                  80
Thr Phe Gly Cys Leu Leu Ala Leu Asp Glu Lys Ser Phe Asn Val Ile
                85                  90                  95
Ala Phe Ser Glu Asn Ala Pro Glu Met Leu Thr Thr Val Ser His Ala
                100                 105                 110
Val Pro Ser Val Asp Asp Pro Arg Leu Gly Ile Gly Thr Asn Val
            115                 120                 125
Arg Ser Leu Phe Ser Asp Gln Gly Ala Thr Ala Leu His Lys Ala Leu
    130                 135                 140
Gly Phe Ala Asp Val Ser Leu Leu Asn Pro Ile Leu Val Gln Cys Lys
145                 150                 155                 160
Thr Ser Gly Lys Pro Phe Tyr Ala Ile Val His Arg Ala Thr Gly Cys
                165                 170                 175
Leu Val Val Asp Phe Glu Pro Val Lys Pro Thr Glu Phe Pro Ala Thr
                180                 185                 190
Ala Ala Gly Ala Leu Gln Ser Tyr Lys Leu Ala Ala Lys Ala Ile Ser
            195                 200                 205
Lys Ile Gln Ser Leu Pro Gly Gly Ser Met Glu Met Leu Cys Asn Thr
    210                 215                 220
Val Val Lys Glu Val Phe Asp Leu Thr Gly Tyr Asp Arg Val Met Ala
225                 230                 235                 240
Tyr Lys Phe His Glu Asp Asp His Gly Glu Val Phe Ser Glu Ile Thr
                245                 250                 255
Lys Pro Gly Leu Glu Pro Tyr Leu Gly Leu His Tyr Pro Ala Thr Asp
                260                 265                 270
Ile Pro Gln Ala Ala Arg Phe Leu Phe Met Lys Asn Lys Val Arg Met
            275                 280                 285
Ile Cys Asp Cys Arg Ala Arg Ser Ile Lys Val Ile Glu Ala Glu Ala
    290                 295                 300
Leu Pro Phe Asp Ile Ser Leu Cys Gly Ser Ala Leu Arg Ala Pro His
305                 310                 315                 320
Ser Cys His Leu Gln Tyr Met Glu Asn Met Asn Ser Ile Ala Ser Leu
                325                 330                 335
```

```
Val Met Ala Val Val Asn Glu Asn Glu Asp Asp Glu Ala Glu
        340                 345                 350

Ser Glu Gln Pro Ala Gln Gln Lys Lys Lys Leu Trp Gly Leu
        355                 360                 365

Leu Val Cys His His Glu Ser Pro Arg Tyr Val Pro Phe Pro Leu Arg
        370                 375                 380

Trp Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
                420                 425                 430

Ile Val Ser Gly Asn Pro Asn Ile Met Asp Leu Val Lys Cys Asp Gly
                435                 440                 445

Ala Ala Leu Leu Tyr Gly Gly Lys Val Trp Arg Leu Arg Asn Ala Pro
        450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
        500                 505                 510

Lys Ile Asn Ser Lys Asp Ile Leu Phe Trp Phe Arg Ser His Thr Ala
        515                 520                 525

Ala Glu Ile Arg Trp Gly Gly Ala Lys Asn Asp Pro Ser Asp Met Asp
        530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
                565                 570                 575

Ile His Ser Leu Gln Leu Ile Leu Arg Gly Thr Leu Asn Asp Ala Ser
                580                 585                 590

Lys Pro Lys Arg Glu Ala Ser Leu Asp Asn Gln Ile Gly Asp Leu Lys
        595                 600                 605

Leu Asp Gly Leu Ala Glu Leu Gln Ala Val Thr Ser Glu Met Val Arg
        610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
                660                 665                 670

Ser Val Pro Val Val Gln Arg Met Leu Tyr Leu Ala Leu Gln Gly Lys
        675                 680                 685

Glu Glu Lys Glu Val Arg Phe Glu Val Lys Thr His Gly Pro Lys Arg
        690                 695                 700

Asp Asp Gly Pro Val Ile Leu Val Val Asn Ala Cys Ala Ser Arg Asp
705                 710                 715                 720

Leu His Asp His Val Gly Val Cys Phe Val Ala Gln Asp Met Thr
                725                 730                 735

Val His Lys Leu Val Met Asp Lys Phe Thr Arg Val Glu Gly Asp Tyr
                740                 745                 750

Lys Ala Ile Ile His Asn Pro Asn Pro Leu Ile Pro Pro Ile Phe Gly
```

```
                755                 760                 765
Ala Asp Glu Phe Gly Trp Cys Ser Glu Trp Asn Ala Ala Met Thr Lys
770                 775                 780

Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
                805                 810                 815

Ala Phe Val Ser Leu Cys Val Leu Ile Asn Ser Ala Leu Ala Gly Glu
            820                 825                 830

Glu Thr Glu Lys Ala Pro Phe Gly Phe Phe Asp Arg Ser Gly Lys Tyr
        835                 840                 845

Ile Glu Cys Leu Leu Ser Ala Asn Arg Lys Glu Asn Glu Gly Gly Leu
    850                 855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
                885                 890                 895

Leu Lys Ala Phe Ser Tyr Met Arg His Ala Ile Asn Asn Pro Leu Ser
            900                 905                 910

Gly Met Leu Tyr Ser Arg Lys Ala Leu Lys Asn Thr Asp Leu Asn Glu
        915                 920                 925

Glu Gln Met Lys Gln Ile His Val Gly Asp Asn Cys His His Gln Ile
    930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
            980                 985                 990

Arg Ile Ser Cys Asn Leu Pro Glu Arg Phe Met Lys Gln Ser Val Tyr
        995                1000                1005

Gly Asp Gly Val Arg Leu Gln Gln Ile Leu Ser Asp Phe Leu Phe
    1010                1015                1020

Ile Ser Val Lys Phe Ser Pro Val Gly Gly Ser Val Glu Ile Ser
    1025                1030                1035

Ser Lys Leu Thr Lys Asn Ser Ile Gly Glu Asn Leu His Leu Ile
    1040                1045                1050

Asp Leu Glu Leu Arg Ile Lys His Gln Gly Leu Gly Val Pro Ala
    1055                1060                1065

Glu Leu Met Ala Gln Met Phe Glu Glu Asp Asn Lys Glu Gln Ser
    1070                1075                1080

Glu Glu Gly Leu Ser Leu Leu Val Ser Arg Asn Leu Leu Arg Leu
    1085                1090                1095

Met Asn Gly Asp Val Arg His Leu Arg Glu Ala Gly Val Ser Thr
    1100                1105                1110

Phe Ile Ile Thr Ala Glu Leu Ala Ser Ala Pro Thr Ala Met Gly
    1115                1120                1125

Gln

<210> SEQ ID NO 5
<211> LENGTH: 1129
<212> TYPE: PRT
<213> ORGANISM: Avena sp.
```

-continued

```
<400> SEQUENCE: 5

Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
            35                  40                  45

Val Glu Ala Gln Arg Asp Gly Pro Pro Val Gln Gln Gly Arg Ser Glu
    50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
            100                 105                 110

Val Pro Ser Val Asp Asp Pro Arg Leu Gly Ile Gly Thr Asn Val
            115                 120                 125

Arg Ser Leu Phe Ser Asp Gln Gly Ala Thr Ala Leu His Lys Ala Leu
    130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
            180                 185                 190

Ala Ala Gly Ala Leu Gln Ser Tyr Lys Leu Ala Ala Lys Ala Ile Ser
            195                 200                 205

Lys Ile Gln Ser Leu Pro Gly Gly Ser Met Glu Met Leu Cys Asn Thr
    210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
            260                 265                 270

Ile Pro Gln Ala Ala Arg Phe Leu Phe Met Lys Asn Lys Val Arg Met
    275                 280                 285

Ile Cys Asp Cys Arg Ala Arg Ser Ile Lys Val Ile Glu Ala Glu Ala
    290                 295                 300

Leu Pro Phe Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
                325                 330                 335

Val Met Ala Val Val Asn Glu Asn Glu Asp Asp Glu Ala Glu
            340                 345                 350

Ser Glu Gln Pro Ala Gln Gln Lys Lys Lys Leu Trp Gly Leu
    355                 360                 365

Leu Val Cys His His Glu Ser Pro Arg Tyr Val Pro Phe Pro Leu Arg
    370                 375                 380

Tyr Ala Cys Glu Ala Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415
```

```
Gln Thr Met Leu Ser Asp Met Leu Phe Arg Glu Ala Ser Pro Leu Thr
            420                 425                 430

Ile Val Ser Gly Asn Pro Asn Ile Met Asp Leu Val Lys Cys Asp Gly
            435                 440                 445

Ala Ala Leu Leu Tyr Gly Gly Lys Val Trp Arg Leu Arg Asn Ala Pro
    450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
            500                 505                 510

Lys Ile Asn Ser Lys Asp Ile Leu Phe Trp Phe Arg Ser His Thr Ala
            515                 520                 525

Ala Glu Ile Arg Trp Gly Gly Ala Lys Asn Asp Pro Ser Asp Met Asp
    530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
                565                 570                 575

Ile His Ser Leu Gln Leu Ile Leu Arg Gly Thr Leu Asn Asp Ala Ser
            580                 585                 590

Lys Pro Lys Arg Glu Ala Ser Leu Asp Asn Gln Ile Gly Asp Leu Lys
            595                 600                 605

Leu Asp Gly Leu Ala Glu Leu Gln Ala Val Thr Ser Glu Met Val Arg
    610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
            660                 665                 670

Ser Val Pro Val Val Gln Arg Met Leu Tyr Leu Ala Leu Gln Gly Lys
            675                 680                 685

Glu Glu Lys Glu Val Arg Phe Glu Val Lys Thr His Gly Pro Lys Arg
    690                 695                 700

Asp Asp Gly Pro Val Ile Leu Val Val Asn Ala Cys Ala Ser Arg Asp
705                 710                 715                 720

Leu His Asp His Val Val Gly Val Cys Phe Val Ala Gln Asp Met Thr
                725                 730                 735

Val His Lys Leu Val Met Asp Lys Phe Thr Arg Val Glu Gly Asp Tyr
            740                 745                 750

Lys Ala Ile Ile His Asn Pro Asn Pro Leu Ile Pro Pro Ile Phe Gly
            755                 760                 765

Ala Asp Glu Phe Gly Trp Cys Ser Glu Trp Asn Ala Ala Met Thr Lys
    770                 775                 780

Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
                805                 810                 815

Ala Phe Val Ser Leu Cys Val Leu Ile Asn Ser Ala Leu Ala Gly Glu
            820                 825                 830
```

-continued

```
Glu Thr Glu Lys Ala Pro Phe Gly Phe Phe Asp Arg Ser Gly Lys Tyr
        835                 840                 845

Ile Glu Cys Leu Leu Ser Ala Asn Arg Lys Glu Asn Glu Gly Gly Leu
    850                 855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
                885                 890                 895

Leu Lys Ala Phe Ser Tyr Met Arg His Ala Ile Asn Asn Pro Leu Ser
            900                 905                 910

Gly Met Leu Tyr Ser Arg Lys Ala Leu Lys Asn Thr Asp Leu Asn Glu
        915                 920                 925

Glu Gln Met Lys Gln Ile His Val Gly Asp Asn Cys His His Gln Ile
    930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
            980                 985                 990

Arg Ile Ser Cys Asn Leu Pro Glu Arg Phe Met Lys Gln Ser Val Tyr
        995                 1000                1005

Gly Asp Gly Val Arg Leu Gln Gln Ile Leu Ser Asp Phe Leu Phe
    1010                1015                1020

Ile Ser Val Lys Phe Ser Pro Val Gly Gly Ser Val Glu Ile Ser
    1025                1030                1035

Ser Lys Leu Thr Lys Asn Ser Ile Gly Glu Asn Leu His Leu Ile
    1040                1045                1050

Asp Leu Glu Leu Arg Ile Lys His Gln Gly Leu Gly Val Pro Ala
    1055                1060                1065

Glu Leu Met Ala Gln Met Phe Glu Glu Asp Asn Lys Glu Gln Ser
    1070                1075                1080

Glu Glu Gly Leu Ser Leu Leu Val Ser Arg Asn Leu Leu Arg Leu
    1085                1090                1095

Met Asn Gly Asp Val Arg His Leu Arg Glu Ala Gly Val Ser Thr
    1100                1105                1110

Phe Ile Ile Thr Ala Glu Leu Ala Ser Ala Pro Thr Ala Met Gly
    1115                1120                1125

Gln
```

```
<210> SEQ ID NO 6
<211> LENGTH: 1129
<212> TYPE: PRT
<213> ORGANISM: Avena sp.

<400> SEQUENCE: 6
```

```
Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
        35                  40                  45

Val Glu Ala Gln Arg Asp Gly Pro Pro Val Gln Gln Gly Arg Ser Glu
    50                  55                  60
```

-continued

```
Lys Val Ile Ala Tyr Leu Gln His Ile Gln Lys Gly Lys Leu Ile Gln
 65                  70                  75                  80

Thr Phe Gly Cys Leu Leu Ala Leu Asp Glu Lys Ser Phe Asn Val Ile
                 85                  90                  95

Ala Phe Ser Glu Asn Ala Pro Glu Met Leu Thr Thr Val Ser His Ala
            100                 105                 110

Val Pro Ser Val Asp Asp Pro Arg Leu Gly Ile Gly Thr Asn Val
        115                 120                 125

Arg Ser Leu Phe Ser Asp Gln Gly Ala Thr Ala Leu His Lys Ala Leu
    130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
            180                 185                 190

Ala Ala Gly Ala Leu Gln Ser Tyr Lys Leu Ala Ala Lys Ala Ile Ser
        195                 200                 205

Lys Ile Gln Ser Leu Pro Gly Gly Ser Met Glu Met Leu Cys Asn Thr
    210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
            260                 265                 270

Ile Pro Gln Ala Ala Arg Phe Leu Phe Met Lys Asn Lys Val Arg Met
        275                 280                 285

Ile Cys Asp Cys Arg Ala Arg Ser Ile Lys Val Ile Glu Ala Glu Ala
    290                 295                 300

Leu Pro Phe Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
                325                 330                 335

Val Met Ala Val Val Val Asn Glu Asn Glu Glu Asp Asp Glu Ala Glu
            340                 345                 350

Ser Glu Gln Pro Ala Gln Gln Lys Lys Lys Leu Trp Gly Leu
    355                 360                 365

Leu Val Cys His His Glu Ser Pro Arg Tyr Val Pro Phe Pro Leu Arg
370                 375                 380

Trp Ala Cys Glu Ala Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
            420                 425                 430

Ile Val Ser Gly Asn Pro Asn Ile Met Asp Leu Val Lys Cys Asp Gly
        435                 440                 445

Ala Ala Leu Leu Tyr Gly Gly Lys Val Trp Arg Leu Arg Asn Ala Pro
    450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
```

-continued

```
                485                 490                 495
Pro Gly Ala Ala Ala Leu Gly Asp Met Ile Cys Gly Met Ala Val Ala
            500                 505                 510
Lys Ile Asn Ser Lys Asp Ile Leu Phe Trp Phe Arg Ser His Thr Ala
            515                 520                 525
Ala Glu Ile Arg Trp Gly Gly Ala Lys Asn Asp Pro Ser Asp Met Asp
            530                 535                 540
Asp Ser Arg Arg Met His Pro Arg Leu Ser Phe Lys Ala Phe Leu Glu
545                 550                 555                 560
Val Val Lys Met Lys Ser Leu Pro Trp Ser Asp Tyr Glu Met Asp Ala
                565                 570                 575
Ile His Ser Leu Gln Leu Ile Leu Arg Gly Thr Leu Asn Asp Ala Ser
                580                 585                 590
Lys Pro Lys Arg Glu Ala Ser Leu Asp Asn Gln Ile Gly Asp Leu Lys
            595                 600                 605
Leu Asp Gly Leu Ala Glu Leu Gln Ala Val Thr Ser Glu Met Val Arg
            610                 615                 620
Leu Met Glu Thr Ala Thr Val Pro Ile Leu Ala Val Asp Gly Asn Gly
625                 630                 635                 640
Leu Val Asn Gly Trp Asn Gln Lys Ala Ala Glu Leu Thr Gly Leu Arg
                645                 650                 655
Val Asp Asp Ala Ile Gly Arg His Ile Leu Thr Leu Val Glu Asp Ser
                660                 665                 670
Ser Val Pro Val Val Gln Arg Met Leu Tyr Leu Ala Leu Gln Gly Lys
            675                 680                 685
Glu Glu Lys Glu Val Arg Phe Glu Val Lys Thr His Gly Pro Lys Arg
            690                 695                 700
Asp Asp Gly Pro Val Ile Leu Val Val Asn Ala Cys Ala Ser Arg Asp
705                 710                 715                 720
Leu His Asp His Val Val Gly Val Cys Phe Val Ala Gln Asp Met Thr
                725                 730                 735
Val His Lys Leu Val Met Asp Lys Phe Thr Arg Val Glu Gly Asp Tyr
                740                 745                 750
Lys Ala Ile Ile His Asn Pro Asn Pro Leu Ile Pro Pro Ile Phe Gly
            755                 760                 765
Ala Asp Glu Phe Gly Trp Cys Ser Glu Trp Asn Ala Ala Met Thr Lys
            770                 775                 780
Leu Thr Gly Trp Asn Arg Asp Glu Val Leu Asp Lys Met Leu Leu Gly
785                 790                 795                 800
Glu Val Phe Asp Ser Ser Asn Ala Ser Cys Pro Leu Lys Asn Arg Asp
                805                 810                 815
Ala Phe Val Ser Leu Cys Val Leu Ile Asn Ser Ala Leu Ala Gly Glu
                820                 825                 830
Glu Thr Glu Lys Ala Pro Phe Gly Phe Phe Asp Arg Ser Gly Lys Tyr
            835                 840                 845
Ile Glu Cys Leu Leu Ser Ala Asn Arg Lys Glu Asn Glu Gly Gly Leu
            850                 855                 860
Ile Thr Gly Val Phe Cys Phe Ile His Val Ala Ser His Glu Leu Gln
865                 870                 875                 880
His Ala Leu Gln Val Gln Gln Ala Ser Glu Gln Thr Ser Leu Lys Arg
                885                 890                 895
Leu Lys Ala Phe Ser Tyr Met Arg His Ala Ile Asn Asn Pro Leu Ser
            900                 905                 910
```

```
Gly Met Leu Tyr Ser Arg Lys Ala Leu Lys Asn Thr Asp Leu Asn Glu
            915                 920                 925

Glu Gln Met Lys Gln Ile His Val Gly Asp Asn Cys His His Gln Ile
        930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
            980                 985                 990

Arg Ile Ser Cys Asn Leu Pro Glu Arg Phe Met Lys Gln Ser Val Tyr
        995                1000                1005

Gly Asp Gly Val Arg Leu Gln Gln Ile Leu Ser Asp Phe Leu Phe
    1010                1015                1020

Ile Ser Val Lys Phe Ser Pro Val Gly Gly Ser Val Glu Ile Ser
    1025                1030                1035

Ser Lys Leu Thr Lys Asn Ser Ile Gly Glu Asn Leu His Leu Ile
    1040                1045                1050

Asp Leu Glu Leu Arg Ile Lys His Gln Gly Leu Gly Val Pro Ala
    1055                1060                1065

Glu Leu Met Ala Gln Met Phe Glu Glu Asp Asn Lys Glu Gln Ser
    1070                1075                1080

Glu Glu Gly Leu Ser Leu Leu Val Ser Arg Asn Leu Leu Arg Leu
    1085                1090                1095

Met Asn Gly Asp Val Arg His Leu Arg Glu Ala Gly Val Ser Thr
    1100                1105                1110

Phe Ile Ile Thr Ala Glu Leu Ala Ser Ala Pro Thr Ala Met Gly
    1115                1120                1125

Gln

<210> SEQ ID NO 7
<211> LENGTH: 1129
<212> TYPE: PRT
<213> ORGANISM: Avena sp.

<400> SEQUENCE: 7

Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
        35                  40                  45

Val Glu Ala Gln Arg Asp Gly Pro Val Gln Gln Gly Arg Ser Glu
    50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
            85                  90                  95

Ala Phe Ser Glu Asn Ala Pro Glu Met Leu Thr Thr Val Ser His Ala
            100                 105                 110

Val Pro Ser Val Asp Asp Pro Arg Leu Gly Ile Gly Thr Asn Val
        115                 120                 125

Arg Ser Leu Phe Ser Asp Gln Gly Ala Thr Ala Leu His Lys Ala Leu
    130                 135                 140
```

```
Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
            165                 170                 175

Leu Val Val Asp Phe Glu Pro Val Lys Pro Thr Glu Phe Pro Ala Thr
                180                 185                 190

Ala Ala Gly Ala Leu Gln Ser Tyr Lys Leu Ala Lys Ala Ile Ser
        195                 200                 205

Lys Ile Gln Ser Leu Pro Gly Gly Ser Met Glu Met Leu Cys Asn Thr
        210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
                260                 265                 270

Ile Pro Gln Ala Ala Arg Phe Leu Phe Met Lys Asn Lys Val Arg Met
        275                 280                 285

Ile Cys Asp Cys Arg Ala Arg Ser Ile Lys Val Ile Glu Ala Glu Ala
        290                 295                 300

Leu Pro Phe Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
                325                 330                 335

Val Met Ala Val Val Val Asn Glu Asn Glu Glu Asp Glu Ala Glu
                340                 345                 350

Ser Glu Gln Pro Ala Gln Gln Lys Lys Lys Leu Trp Gly Leu
        355                 360                 365

Leu Val Cys His His Glu Ser Pro Arg Tyr Val Pro Phe Pro Leu Arg
        370                 375                 380

Tyr Ala Cys Glu Tyr Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
            420                 425                 430

Ile Val Ser Gly Asn Pro Asn Ile Met Asp Leu Val Lys Cys Asp Gly
        435                 440                 445

Ala Ala Leu Leu Tyr Gly Gly Lys Val Trp Arg Leu Arg Asn Ala Pro
450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
                500                 505                 510

Lys Ile Asn Ser Lys Asp Ile Leu Phe Trp Phe Arg Ser His Thr Ala
        515                 520                 525

Ala Glu Ile Arg Trp Gly Gly Ala Lys Asn Asp Pro Ser Asp Met Asp
        530                 535                 540

Asp Ser Arg Arg Met His Pro Arg Leu Ser Phe Lys Ala Phe Leu Glu
545                 550                 555                 560
```

-continued

```
Val Val Lys Met Lys Ser Leu Pro Trp Ser Asp Tyr Glu Met Asp Ala
                565                 570                 575

Ile His Ser Leu Gln Leu Ile Leu Arg Gly Thr Leu Asn Asp Ala Ser
            580                 585                 590

Lys Pro Lys Arg Glu Ala Ser Leu Asp Asn Gln Ile Gly Asp Leu Lys
        595                 600                 605

Leu Asp Gly Leu Ala Glu Leu Gln Ala Val Thr Ser Glu Met Val Arg
    610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
            660                 665                 670

Ser Val Pro Val Val Gln Arg Met Leu Tyr Leu Ala Leu Gln Gly Lys
        675                 680                 685

Glu Glu Lys Glu Val Arg Phe Glu Val Lys Thr His Gly Pro Lys Arg
    690                 695                 700

Asp Asp Gly Pro Val Ile Leu Val Val Asn Ala Cys Ala Ser Arg Asp
705                 710                 715                 720

Leu His Asp His Val Val Gly Val Cys Phe Val Ala Gln Asp Met Thr
                725                 730                 735

Val His Lys Leu Val Met Asp Lys Phe Thr Arg Val Glu Gly Asp Tyr
            740                 745                 750

Lys Ala Ile Ile His Asn Pro Asn Pro Leu Ile Pro Pro Ile Phe Gly
        755                 760                 765

Ala Asp Glu Phe Gly Trp Cys Ser Glu Trp Asn Ala Ala Met Thr Lys
    770                 775                 780

Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
                805                 810                 815

Ala Phe Val Ser Leu Cys Val Leu Ile Asn Ser Ala Leu Ala Gly Glu
            820                 825                 830

Glu Thr Glu Lys Ala Pro Phe Gly Phe Phe Asp Arg Ser Gly Lys Tyr
        835                 840                 845

Ile Glu Cys Leu Leu Ser Ala Asn Arg Lys Glu Asn Glu Gly Gly Leu
    850                 855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
                885                 890                 895

Leu Lys Ala Phe Ser Tyr Met Arg His Ala Ile Asn Asn Pro Leu Ser
            900                 905                 910

Gly Met Leu Tyr Ser Arg Lys Ala Leu Lys Asn Thr Asp Leu Asn Glu
        915                 920                 925

Glu Gln Met Lys Gln Ile His Val Gly Asp Asn Cys His His Gln Ile
    930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
```

```
                    980              985              990
Arg Ile Ser Cys Asn Leu Pro Glu  Arg Phe Met Lys Gln  Ser Val Tyr
                995              1000             1005

Gly Asp Gly Val Arg Leu Gln  Gln Ile Leu Ser Asp  Phe Leu Phe
        1010             1015             1020

Ile Ser Val Lys Phe Ser Pro  Val Gly Gly Ser Val  Glu Ile Ser
        1025             1030             1035

Ser Lys Leu Thr Lys Asn Ser  Ile Gly Glu Asn Leu  His Leu Ile
        1040             1045             1050

Asp Leu Glu Leu Arg Ile Lys  His Gln Gly Leu Gly  Val Pro Ala
        1055             1060             1065

Glu Leu Met Ala Gln Met Phe  Glu Glu Asp Asn Lys  Glu Gln Ser
        1070             1075             1080

Glu Glu Gly Leu Ser Leu Leu  Val Ser Arg Asn Leu  Leu Arg Leu
        1085             1090             1095

Met Asn Gly Asp Val Arg His  Leu Arg Glu Ala Gly  Val Ser Thr
        1100             1105             1110

Phe Ile Ile Thr Ala Glu Leu  Ala Ser Ala Pro Thr  Ala Met Gly
        1115             1120             1125

Gln

<210> SEQ ID NO 8
<211> LENGTH: 1129
<212> TYPE: PRT
<213> ORGANISM: Avena sp.

<400> SEQUENCE: 8

Met Ser Ser Ser Arg Pro Ala Ser  Ser Ser Ser Arg Asn Arg Gln
1               5                10              15

Ser Ser Gln Ala Arg Val Leu Ala  Gln Thr Thr Leu Asp Ala Glu Leu
                20               25              30

Asn Ala Glu Tyr Glu Glu Ser Gly  Asp Ser Phe Asp Tyr Ser Lys Leu
        35               40              45

Val Glu Ala Gln Arg Asp Gly Pro  Pro Val Gln Gln Gly Arg Ser Glu
50               55              60

Lys Val Ile Ala Tyr Leu Gln His  Ile Gln Lys Gly Lys Leu Ile Gln
65               70              75              80

Thr Phe Gly Cys Leu Leu Ala Leu  Asp Glu Lys Ser Phe Asn Val Ile
                85               90              95

Ala Phe Ser Glu Asn Ala Pro Glu  Met Leu Thr Thr Val Ser His Ala
                100              105             110

Val Pro Ser Val Asp Asp Pro Arg  Leu Gly Ile Gly Thr Asn Val
        115              120             125

Arg Ser Leu Phe Ser Asp Gln Gly  Ala Thr Ala Leu His Lys Ala Leu
        130              135             140

Gly Phe Ala Asp Val Ser Leu Leu  Asn Pro Ile Leu Val Gln Cys Lys
145              150             155             160

Thr Ser Gly Lys Pro Phe Tyr Ala  Ile Val His Arg Ala Thr Gly Cys
                165              170             175

Leu Val Val Asp Phe Glu Pro Val  Lys Pro Thr Glu Phe Pro Ala Thr
                180              185             190

Ala Ala Gly Ala Leu Gln Ser Tyr  Lys Leu Ala Ala Lys Ala Ile Ser
        195              200             205

Lys Ile Gln Ser Leu Pro Gly Gly Ser Met Glu Met Leu Cys Asn Thr
```

```
                210                 215                 220
Val Val Lys Glu Val Phe Asp Leu Thr Gly Tyr Asp Arg Val Met Ala
225                 230                 235                 240

Tyr Lys Phe His Glu Asp His Gly Glu Val Phe Ser Glu Ile Thr
                245                 250                 255

Lys Pro Gly Leu Glu Pro Tyr Leu Gly Leu His Tyr Pro Ala Thr Asp
                260                 265                 270

Ile Pro Gln Ala Ala Arg Phe Leu Phe Met Lys Asn Lys Val Arg Met
                275                 280                 285

Ile Cys Asp Cys Arg Ala Arg Ser Ile Lys Val Ile Glu Ala Glu Ala
290                 295                 300

Leu Pro Arg Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
                325                 330                 335

Val Met Ala Val Val Asn Glu Asn Glu Glu Asp Asp Glu Ala Glu
                340                 345                 350

Ser Glu Gln Pro Ala Gln Gln Lys Lys Lys Leu Trp Gly Leu
                355                 360                 365

Leu Val Ala His His Glu Ser Pro Arg Tyr Val Pro Phe Pro Leu Arg
370                 375                 380

Tyr Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
                420                 425                 430

Ile Val Ser Gly Asn Pro Asn Ile Met Asp Leu Val Lys Cys Asp Gly
                435                 440                 445

Ala Ala Leu Leu Tyr Gly Gly Lys Val Trp Arg Leu Arg Asn Ala Pro
                450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
                500                 505                 510

Lys Ile Asn Ser Lys Asp Ile Leu Phe Trp Phe Arg Ser His Thr Ala
                515                 520                 525

Ala Glu Ile Arg Trp Gly Gly Ala Lys Asn Asp Pro Ser Asp Met Asp
530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
                565                 570                 575

Ile His Ser Leu Gln Leu Ile Leu Arg Gly Thr Leu Asn Asp Ala Ser
                580                 585                 590

Lys Pro Lys Arg Glu Ala Ser Leu Asp Asn Gln Ile Gly Asp Leu Lys
                595                 600                 605

Leu Asp Gly Leu Ala Glu Leu Gln Ala Val Thr Ser Glu Met Val Arg
                610                 615                 620

Leu Met Glu Thr Ala Thr Val Pro Ile Leu Ala Val Asp Gly Asn Gly
625                 630                 635                 640
```

-continued

Leu Val Asn Gly Trp Asn Gln Lys Ala Ala Glu Leu Thr Gly Leu Arg
            645                 650                 655

Val Asp Asp Ala Ile Gly Arg His Ile Leu Thr Leu Val Glu Asp Ser
        660                 665                 670

Ser Val Pro Val Val Gln Arg Met Leu Tyr Leu Ala Leu Gln Gly Lys
    675                 680                 685

Glu Glu Lys Glu Val Arg Phe Glu Val Lys Thr His Gly Pro Lys Arg
690                 695                 700

Asp Asp Gly Pro Val Ile Leu Val Val Asn Ala Cys Ala Ser Arg Asp
705                 710                 715                 720

Leu His Asp His Val Gly Val Cys Phe Val Ala Gln Asp Met Thr
            725                 730                 735

Val His Lys Leu Val Met Asp Lys Phe Thr Arg Val Glu Gly Asp Tyr
        740                 745                 750

Lys Ala Ile Ile His Asn Pro Asn Pro Leu Ile Pro Pro Ile Phe Gly
            755                 760                 765

Ala Asp Glu Phe Gly Trp Cys Ser Glu Trp Asn Ala Ala Met Thr Lys
770                 775                 780

Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
                805                 810                 815

Ala Phe Val Ser Leu Cys Val Leu Ile Asn Ser Ala Leu Ala Gly Glu
            820                 825                 830

Glu Thr Glu Lys Ala Pro Phe Gly Phe Phe Asp Arg Ser Gly Lys Tyr
        835                 840                 845

Ile Glu Cys Leu Leu Ser Ala Asn Arg Lys Glu Asn Glu Gly Gly Leu
    850                 855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
            885                 890                 895

Leu Lys Ala Phe Ser Tyr Met Arg His Ala Ile Asn Asn Pro Leu Ser
            900                 905                 910

Gly Met Leu Tyr Ser Arg Lys Ala Leu Lys Asn Thr Asp Leu Asn Glu
        915                 920                 925

Glu Gln Met Lys Gln Ile His Val Gly Asp Asn Cys His His Gln Ile
    930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
            965                 970                 975

Val Ala Ala Val Ser Gln Val Leu Ile Thr Cys Gln Gly Lys Gly Ile
            980                 985                 990

Arg Ile Ser Cys Asn Leu Pro Glu Arg Phe Met Lys Gln Ser Val Tyr
        995                 1000                1005

Gly Asp Gly Val Arg Leu Gln Gln Ile Leu Ser Asp Phe Leu Phe
    1010                1015                1020

Ile Ser Val Lys Phe Ser Pro Val Gly Gly Ser Val Glu Ile Ser
    1025                1030                1035

Ser Lys Leu Thr Lys Asn Ser Ile Gly Glu Asn Leu His Leu Ile
    1040                1045                1050

```
Asp Leu Glu Leu Arg Ile Lys His Gln Gly Leu Gly Val Pro Ala
    1055                1060                1065

Glu Leu Met Ala Gln Met Phe Glu Asp Asn Lys Glu Gln Ser
    1070                1075                1080

Glu Glu Gly Leu Ser Leu Leu Val Ser Arg Asn Leu Leu Arg Leu
    1085                1090                1095

Met Asn Gly Asp Val Arg His Leu Arg Glu Ala Gly Val Ser Thr
    1100                1105                1110

Phe Ile Ile Thr Ala Glu Leu Ala Ser Ala Pro Thr Ala Met Gly
    1115                1120                1125

Gln

<210> SEQ ID NO 9
<211> LENGTH: 1129
<212> TYPE: PRT
<213> ORGANISM: Avena sp.

<400> SEQUENCE: 9

Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Ser Gly Asp Ser Phe Asp Tyr Ser Lys Leu
            35                  40                  45

Val Glu Ala Gln Arg Asp Gly Pro Pro Val Gln Gln Gly Arg Ser Glu
    50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                    85                  90                  95

Ala Phe Ser Glu Asn Ala Pro Glu Met Leu Thr Thr Val Ser His Ala
                100                 105                 110

Val Pro Ser Val Asp Asp Pro Arg Leu Gly Ile Gly Thr Asn Val
    115                 120                 125

Arg Ser Leu Phe Ser Asp Gln Gly Ala Thr Ala Leu His Lys Ala Leu
130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                    165                 170                 175

Leu Val Val Asp Phe Glu Pro Val Lys Pro Thr Glu Phe Pro Ala Thr
                    180                 185                 190

Ala Ala Gly Ala Leu Gln Ser Tyr Lys Leu Ala Ala Lys Ala Ile Ser
        195                 200                 205

Lys Ile Gln Ser Leu Pro Gly Gly Ser Met Glu Met Leu Cys Asn Thr
210                 215                 220

Val Val Lys Glu Val Phe Asp Leu Thr Gly Tyr Asp Arg Val Met Ala
225                 230                 235                 240

Tyr Lys Phe His Glu Asp His Gly Glu Val Phe Ser Glu Ile Thr
                    245                 250                 255

Lys Pro Gly Leu Glu Pro Tyr Leu Gly Leu His Tyr Pro Ala Thr Asp
                260                 265                 270

Ile Pro Gln Ala Ala Arg Phe Leu Phe Met Lys Asn Lys Val Arg Met
        275                 280                 285
```

```
Ile Cys Asp Cys Arg Ala Arg Ser Ile Lys Val Ile Glu Ala Glu Ala
290                 295                 300

Leu Pro Arg Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
                325                 330                 335

Val Met Ala Val Val Asn Glu Asn Glu Glu Asp Asp Glu Ala Glu
            340                 345                 350

Ser Glu Gln Pro Ala Gln Gln Lys Lys Lys Leu Trp Gly Leu
        355                 360                 365

Leu Val Ala His His Glu Ser Pro Arg Tyr Val Pro Phe Pro Leu Arg
370                 375                 380

Trp Ala Cys Glu Ala Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
                420                 425                 430

Ile Val Ser Gly Asn Pro Asn Ile Met Asp Leu Val Lys Cys Asp Gly
            435                 440                 445

Ala Ala Leu Leu Tyr Gly Gly Lys Val Trp Arg Leu Arg Asn Ala Pro
450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
            500                 505                 510

Lys Ile Asn Ser Lys Asp Ile Leu Phe Trp Phe Arg Ser His Thr Ala
            515                 520                 525

Ala Glu Ile Arg Trp Gly Gly Ala Lys Asn Asp Pro Ser Asp Met Asp
530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
                565                 570                 575

Ile His Ser Leu Gln Leu Ile Leu Arg Gly Thr Leu Asn Asp Ala Ser
            580                 585                 590

Lys Pro Lys Arg Glu Ala Ser Leu Asp Asn Gln Ile Gly Asp Leu Lys
        595                 600                 605

Leu Asp Gly Leu Ala Glu Leu Gln Ala Val Thr Ser Glu Met Val Arg
610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
            660                 665                 670

Ser Val Pro Val Val Gln Arg Met Leu Tyr Leu Ala Leu Gln Gly Lys
        675                 680                 685

Glu Glu Lys Glu Val Arg Phe Glu Val Lys Thr His Gly Pro Lys Arg
690                 695                 700

Asp Asp Gly Pro Val Ile Leu Val Val Asn Ala Cys Ala Ser Arg Asp
```

```
                705                 710                 715                 720
Leu His Asp His Val Gly Val Cys Phe Val Ala Gln Asp Met Thr
                725                 730                 735
Val His Lys Leu Val Met Asp Lys Phe Thr Arg Val Glu Gly Asp Tyr
                740                 745                 750
Lys Ala Ile Ile His Asn Pro Asn Pro Leu Ile Pro Pro Ile Phe Gly
                755                 760                 765
Ala Asp Glu Phe Gly Trp Cys Ser Glu Trp Asn Ala Ala Met Thr Lys
    770                 775                 780
Leu Thr Gly Trp Asn Arg Asp Glu Val Leu Asp Lys Met Leu Leu Gly
785                 790                 795                 800
Glu Val Phe Asp Ser Ser Asn Ala Ser Cys Pro Leu Lys Asn Arg Asp
                805                 810                 815
Ala Phe Val Ser Leu Cys Val Leu Ile Asn Ser Ala Leu Ala Gly Glu
                820                 825                 830
Glu Thr Glu Lys Ala Pro Phe Gly Phe Asp Arg Ser Gly Lys Tyr
                835                 840                 845
Ile Glu Cys Leu Leu Ser Ala Asn Arg Lys Glu Asn Glu Gly Gly Leu
    850                 855                 860
Ile Thr Gly Val Phe Cys Phe Ile His Val Ala Ser His Glu Leu Gln
865                 870                 875                 880
His Ala Leu Gln Val Gln Gln Ala Ser Glu Gln Thr Ser Leu Lys Arg
                885                 890                 895
Leu Lys Ala Phe Ser Tyr Met Arg His Ala Ile Asn Asn Pro Leu Ser
                900                 905                 910
Gly Met Leu Tyr Ser Arg Lys Ala Leu Lys Asn Thr Asp Leu Asn Glu
                915                 920                 925
Glu Gln Met Lys Gln Ile His Val Gly Asp Asn Cys His His Gln Ile
                930                 935                 940
Asn Lys Ile Leu Ala Asp Leu Asp Gln Asp Ser Ile Thr Glu Lys Ser
945                 950                 955                 960
Ser Cys Leu Asp Leu Glu Met Ala Glu Phe Leu Leu Gln Asp Val Val
                965                 970                 975
Val Ala Ala Val Ser Gln Val Leu Ile Thr Cys Gln Gly Lys Gly Ile
                980                 985                 990
Arg Ile Ser Cys Asn Leu Pro Glu Arg Phe Met Lys Gln Ser Val Tyr
    995                 1000                1005
Gly Asp Gly Val Arg Leu Gln Ile Leu Ser Asp Phe Leu Phe
    1010                1015                1020
Ile Ser Val Lys Phe Ser Pro Val Gly Gly Ser Val Glu Ile Ser
    1025                1030                1035
Ser Lys Leu Thr Lys Asn Ser Ile Gly Glu Asn Leu His Leu Ile
    1040                1045                1050
Asp Leu Glu Leu Arg Ile Lys His Gln Gly Leu Gly Val Pro Ala
    1055                1060                1065
Glu Leu Met Ala Gln Met Phe Glu Glu Asp Asn Lys Glu Gln Ser
    1070                1075                1080
Glu Glu Gly Leu Ser Leu Leu Val Ser Arg Asn Leu Leu Arg Leu
    1085                1090                1095
Met Asn Gly Asp Val Arg His Leu Arg Glu Ala Gly Val Ser Thr
    1100                1105                1110
Phe Ile Ile Thr Ala Glu Leu Ala Ser Ala Pro Thr Ala Met Gly
    1115                1120                1125
```

Gln

<210> SEQ ID NO 10
<211> LENGTH: 1129
<212> TYPE: PRT
<213> ORGANISM: Avena sp.

<400> SEQUENCE: 10

```
Met Ser Ser Ser Arg Pro Ala Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
        35                  40                  45

Val Glu Ala Gln Arg Asp Gly Pro Pro Val Gln Gln Gly Arg Ser Glu
    50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
            100                 105                 110

Val Pro Ser Val Asp Asp Pro Arg Leu Gly Ile Gly Thr Asn Val
        115                 120                 125

Arg Ser Leu Phe Ser Asp Gln Gly Ala Thr Ala Leu His Lys Ala Leu
130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
            180                 185                 190

Ala Ala Gly Ala Leu Gln Ser Tyr Lys Leu Ala Ala Lys Ala Ile Ser
        195                 200                 205

Lys Ile Gln Ser Leu Pro Gly Gly Ser Met Glu Met Leu Cys Asn Thr
    210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
            260                 265                 270

Ile Pro Gln Ala Ala Arg Phe Leu Phe Met Lys Asn Lys Val Arg Met
        275                 280                 285

Ile Cys Asp Cys Arg Ala Arg Ser Ile Lys Val Ile Glu Ala Glu Ala
    290                 295                 300

Leu Pro Trp Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
                325                 330                 335

Val Met Ala Val Val Val Asn Glu Asn Glu Glu Asp Asp Glu Ala Glu
            340                 345                 350

Ser Glu Gln Pro Ala Gln Gln Lys Lys Lys Leu Trp Gly Leu
        355                 360                 365
```

```
Leu Val Cys His His Glu Ser Pro Arg Tyr Val Pro Phe Pro Leu Arg
    370                 375                 380

Ala Ala Cys Glu Ala Leu Ala Gln Val Phe Ala Val His Val Asn Arg
385                 390                 395                 400

Glu Phe Glu Leu Glu Lys Gln Leu Arg Glu Lys Asn Ile Leu Lys Met
                    405                 410                 415

Gln Thr Met Leu Ser Asp Met Leu Phe Arg Glu Ala Ser Pro Leu Thr
                420                 425                 430

Ile Val Ser Gly Asn Pro Asn Ile Met Asp Leu Val Lys Cys Asp Gly
            435                 440                 445

Ala Ala Leu Leu Tyr Gly Gly Lys Val Trp Arg Leu Arg Asn Ala Pro
450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
                500                 505                 510

Lys Ile Asn Ser Lys Asp Ile Leu Phe Trp Phe Arg Ser His Thr Ala
            515                 520                 525

Ala Glu Ile Arg Trp Gly Gly Ala Lys Asn Asp Pro Ser Asp Met Asp
530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
                565                 570                 575

Ile His Ser Leu Gln Leu Ile Leu Arg Gly Thr Leu Asn Asp Ala Ser
                580                 585                 590

Lys Pro Lys Arg Glu Ala Ser Leu Asp Asn Gln Ile Gly Asp Leu Lys
            595                 600                 605

Leu Asp Gly Leu Ala Glu Leu Gln Ala Val Thr Ser Glu Met Val Arg
610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
                660                 665                 670

Ser Val Pro Val Val Gln Arg Met Leu Tyr Leu Ala Leu Gln Gly Lys
            675                 680                 685

Glu Glu Lys Glu Val Arg Phe Glu Val Lys Thr His Gly Pro Lys Arg
690                 695                 700

Asp Asp Gly Pro Val Ile Leu Val Val Asn Ala Cys Ala Ser Arg Asp
705                 710                 715                 720

Leu His Asp His Val Val Gly Val Cys Phe Val Ala Gln Asp Met Thr
                725                 730                 735

Val His Lys Leu Val Met Asp Lys Phe Thr Arg Val Glu Gly Asp Tyr
                740                 745                 750

Lys Ala Ile Ile His Asn Pro Asn Pro Leu Ile Pro Pro Ile Phe Gly
            755                 760                 765

Ala Asp Glu Phe Gly Trp Cys Ser Glu Trp Asn Ala Ala Met Thr Lys
770                 775                 780
```

-continued

```
Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
            805                 810                 815

Ala Phe Val Ser Leu Cys Val Leu Ile Asn Ser Ala Leu Ala Gly Glu
        820                 825                 830

Glu Thr Glu Lys Ala Pro Phe Gly Phe Phe Asp Arg Ser Gly Lys Tyr
    835                 840                 845

Ile Glu Cys Leu Leu Ser Ala Asn Arg Lys Glu Asn Glu Gly Gly Leu
850                 855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
            885                 890                 895

Leu Lys Ala Phe Ser Tyr Met Arg His Ala Ile Asn Asn Pro Leu Ser
        900                 905                 910

Gly Met Leu Tyr Ser Arg Lys Ala Leu Lys Asn Thr Asp Leu Asn Glu
    915                 920                 925

Glu Gln Met Lys Gln Ile His Val Gly Asp Asn Cys His His Gln Ile
930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
            965                 970                 975

Val Ala Ala Val Ser Gln Val Leu Ile Thr Cys Gln Gly Lys Gly Ile
        980                 985                 990

Arg Ile Ser Cys Asn Leu Pro Glu Arg Phe Met Lys Gln Ser Val Tyr
    995                 1000                1005

Gly Asp Gly Val Arg Leu Gln Gln Ile Leu Ser Asp Phe Leu Phe
    1010                1015                1020

Ile Ser Val Lys Phe Ser Pro Val Gly Gly Ser Val Glu Ile Ser
    1025                1030                1035

Ser Lys Leu Thr Lys Asn Ser Ile Gly Glu Asn Leu His Leu Ile
    1040                1045                1050

Asp Leu Glu Leu Arg Ile Lys His Gln Gly Leu Gly Val Pro Ala
    1055                1060                1065

Glu Leu Met Ala Gln Met Phe Glu Glu Asp Asn Lys Glu Gln Ser
    1070                1075                1080

Glu Glu Gly Leu Ser Leu Leu Val Ser Arg Asn Leu Leu Arg Leu
    1085                1090                1095

Met Asn Gly Asp Val Arg His Leu Arg Glu Ala Gly Val Ser Thr
    1100                1105                1110

Phe Ile Ile Thr Ala Glu Leu Ala Ser Ala Pro Thr Ala Met Gly
    1115                1120                1125

Gln
```

```
<210> SEQ ID NO 11
<211> LENGTH: 1129
<212> TYPE: PRT
<213> ORGANISM: Avena sp.

<400> SEQUENCE: 11

Met Ser Ser Ser Arg Pro Ala Ser Ser Ser Ser Arg Asn Arg Gln
1               5                   10                  15
```

-continued

```
Ser Ser Gln Ala Arg Val Leu Ala Gln Thr Thr Leu Asp Ala Glu Leu
         20                  25                  30

Asn Ala Glu Tyr Glu Glu Ser Gly Asp Ser Phe Asp Tyr Ser Lys Leu
         35                  40                  45

Val Glu Ala Gln Arg Asp Gly Pro Pro Val Gln Gln Gly Arg Ser Glu
 50                  55                  60

Lys Val Ile Ala Tyr Leu Gln His Ile Gln Lys Gly Lys Leu Ile Gln
 65                  70                  75                  80

Thr Phe Gly Cys Leu Leu Ala Leu Asp Glu Lys Ser Phe Asn Val Ile
                 85                  90                  95

Ala Phe Ser Glu Asn Ala Pro Glu Met Leu Thr Thr Val Ser His Ala
             100                 105                 110

Val Pro Ser Val Asp Asp Pro Arg Leu Gly Ile Gly Thr Asn Val
             115                 120                 125

Arg Ser Leu Phe Ser Asp Gln Gly Ala Thr Ala Leu His Lys Ala Leu
130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
            180                 185                 190

Ala Ala Gly Ala Leu Gln Ser Tyr Lys Leu Ala Ala Lys Ala Ile Ser
            195                 200                 205

Lys Ile Gln Ser Leu Pro Gly Gly Ser Met Glu Met Leu Cys Asn Thr
210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
            260                 265                 270

Ile Pro Gln Ala Ala Arg Phe Leu Phe Met Lys Asn Lys Val Arg Met
            275                 280                 285

Ile Cys Asp Cys Arg Ala Arg Ser Ile Lys Val Ile Glu Ala Glu Ala
290                 295                 300

Leu Pro Phe Lys Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
                325                 330                 335

Val Met Ala Val Val Asn Glu Asn Glu Glu Asp Asp Glu Ala Glu
            340                 345                 350

Ser Glu Gln Pro Ala Gln Gln Lys Lys Lys Leu Trp Gly Leu
            355                 360                 365

Leu Val Cys His His Glu Ser Pro Arg Tyr Val Pro Phe Pro Leu Arg
370                 375                 380

Tyr Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
            420                 425                 430

Ile Val Ser Gly Asn Pro Asn Ile Met Asp Leu Val Lys Cys Asp Gly
```

```
                     435                 440                 445
Ala Ala Leu Leu Tyr Gly Gly Lys Val Trp Arg Leu Arg Asn Ala Pro
            450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
            500                 505                 510

Lys Ile Asn Ser Lys Asp Ile Leu Phe Trp Phe Arg Ser His Thr Ala
            515                 520                 525

Ala Glu Ile Arg Trp Gly Gly Ala Lys Asn Asp Pro Ser Asp Met Asp
            530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
                565                 570                 575

Ile His Ser Leu Gln Leu Ile Leu Arg Gly Thr Leu Asn Asp Ala Ser
            580                 585                 590

Lys Pro Lys Arg Glu Ala Ser Leu Asp Asn Gln Ile Gly Asp Leu Lys
            595                 600                 605

Leu Asp Gly Leu Ala Glu Leu Gln Ala Val Thr Ser Glu Met Val Arg
    610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
                660                 665                 670

Ser Val Pro Val Val Gln Arg Met Leu Tyr Leu Ala Leu Gln Gly Lys
            675                 680                 685

Glu Glu Lys Glu Val Arg Phe Glu Val Lys Thr His Gly Pro Lys Arg
    690                 695                 700

Asp Asp Gly Pro Val Ile Leu Val Val Asn Ala Cys Ala Ser Arg Asp
705                 710                 715                 720

Leu His Asp His Val Val Gly Val Cys Phe Val Ala Gln Asp Met Thr
                725                 730                 735

Val His Lys Leu Val Met Asp Lys Phe Thr Arg Val Glu Gly Asp Tyr
            740                 745                 750

Lys Ala Ile Ile His Asn Pro Asn Pro Leu Ile Pro Pro Ile Phe Gly
            755                 760                 765

Ala Asp Glu Phe Gly Trp Cys Ser Glu Trp Asn Ala Ala Met Thr Lys
770                 775                 780

Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
                805                 810                 815

Ala Phe Val Ser Leu Cys Val Leu Ile Asn Ser Ala Leu Ala Gly Glu
                820                 825                 830

Glu Thr Glu Lys Ala Pro Phe Gly Phe Phe Asp Arg Ser Gly Lys Tyr
            835                 840                 845

Ile Glu Cys Leu Leu Ser Ala Asn Arg Lys Glu Asn Glu Gly Gly Leu
            850                 855                 860
```

```
Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
                885                 890                 895

Leu Lys Ala Phe Ser Tyr Met Arg His Ala Ile Asn Asn Pro Leu Ser
            900                 905                 910

Gly Met Leu Tyr Ser Arg Lys Ala Leu Lys Asn Thr Asp Leu Asn Glu
        915                 920                 925

Glu Gln Met Lys Gln Ile His Val Gly Asp Asn Cys His His Gln Ile
    930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Gln Asp Val Val
                965                 970                 975

Val Ala Ala Val Ser Gln Val Leu Ile Thr Cys Gln Gly Lys Gly Ile
            980                 985                 990

Arg Ile Ser Cys Asn Leu Pro Glu  Arg Phe Met Lys Gln  Ser Val Tyr
            995            1000                 1005

Gly Asp  Gly Val Arg Leu Gln  Gln Ile Leu Ser Asp  Phe Leu Phe
   1010              1015                1020

Ile Ser  Val Lys Phe Ser Pro  Val Gly Gly Ser Val  Glu Ile Ser
   1025              1030                1035

Ser Lys  Leu Thr Lys Asn Ser  Ile Gly Glu Asn Leu  His Leu Ile
   1040              1045                1050

Asp Leu  Glu Leu Arg Ile Lys  His Gln Gly Leu Gly  Val Pro Ala
   1055              1060                1065

Glu Leu  Met Ala Gln Met Phe  Glu Glu Asp Asn Lys  Glu Gln Ser
   1070              1075                1080

Glu Glu  Gly Leu Ser Leu Leu  Val Ser Arg Asn Leu  Leu Arg Leu
   1085              1090                1095

Met Asn  Gly Asp Val Arg His  Leu Arg Glu Ala Gly  Val Ser Thr
   1100              1105                1110

Phe Ile  Ile Thr Ala Glu Leu  Ala Ser Ala Pro Thr  Ala Met Gly
   1115              1120                1125

Gln

<210> SEQ ID NO 12
<211> LENGTH: 1129
<212> TYPE: PRT
<213> ORGANISM: Avena sp.

<400> SEQUENCE: 12

Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
        35                  40                  45

Val Glu Ala Gln Arg Asp Gly Pro Pro Val Gln Gln Gly Arg Ser Glu
    50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95
```

-continued

```
Ala Phe Ser Glu Asn Ala Pro Glu Met Leu Thr Thr Val Ser His Ala
                100                 105                 110

Val Pro Ser Val Asp Asp Pro Arg Leu Gly Ile Gly Thr Asn Val
        115                 120                 125

Arg Ser Leu Phe Ser Asp Gln Gly Ala Thr Ala Leu His Lys Ala Leu
    130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
                180                 185                 190

Ala Ala Gly Ala Leu Gln Ser Tyr Lys Leu Ala Ala Lys Ala Ile Ser
            195                 200                 205

Lys Ile Gln Ser Leu Pro Gly Gly Ser Met Glu Met Leu Cys Asn Thr
    210                 215                 220

Val Val Lys Glu Val Phe Asp Leu Thr Gly Tyr Asp Arg Val Met Ala
225                 230                 235                 240

Tyr Lys Phe His Glu Asp His Gly Glu Val Phe Ser Glu Ile Thr
                245                 250                 255

Lys Pro Gly Leu Glu Pro Phe Leu Gly Leu His Tyr Pro Ala Thr Asp
                260                 265                 270

Ile Pro Gln Ala Ala Arg Phe Leu Phe Met Lys Asn Lys Val Arg Met
            275                 280                 285

Ile Cys Asp Cys Arg Ala Arg Ser Ile Lys Val Ile Glu Ala Glu Ala
        290                 295                 300

Leu Pro Phe Asp Ile Ser Leu Cys Gly Ser Ala Leu Arg Ala Pro His
305                 310                 315                 320

Ser Cys His Leu Gln Tyr Met Glu Asn Met Asn Ser Ile Ala Ser Leu
                325                 330                 335

Val Met Ala Val Val Val Asn Glu Asn Glu Glu Asp Asp Glu Ala Glu
            340                 345                 350

Ser Glu Gln Pro Ala Gln Gln Lys Lys Lys Leu Trp Gly Leu
    355                 360                 365

Leu Val Cys His His Glu Ser Pro Arg Tyr Val Pro Phe Pro Leu Arg
    370                 375                 380

Tyr Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
            420                 425                 430

Ile Val Ser Gly Asn Pro Asn Ile Met Asp Leu Val Lys Cys Asp Gly
        435                 440                 445

Ala Ala Leu Leu Tyr Gly Gly Lys Val Trp Arg Leu Arg Asn Ala Pro
    450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
            500                 505                 510
```

```
Lys Ile Asn Ser Lys Asp Ile Leu Phe Trp Phe Arg Ser His Thr Ala
        515                 520                 525
Ala Glu Ile Arg Trp Gly Gly Ala Lys Asn Asp Pro Ser Asp Met Asp
    530                 535                 540
Asp Ser Arg Arg Met His Pro Arg Leu Ser Phe Lys Ala Phe Leu Glu
545                 550                 555                 560
Val Val Lys Met Lys Ser Leu Pro Trp Ser Asp Tyr Glu Met Asp Ala
                565                 570                 575
Ile His Ser Leu Gln Leu Ile Leu Arg Gly Thr Leu Asn Asp Ala Ser
            580                 585                 590
Lys Pro Lys Arg Glu Ala Ser Leu Asp Asn Gln Ile Gly Asp Leu Lys
        595                 600                 605
Leu Asp Gly Leu Ala Glu Leu Gln Ala Val Thr Ser Glu Met Val Arg
    610                 615                 620
Leu Met Glu Thr Ala Thr Val Pro Ile Leu Ala Val Asp Gly Asn Gly
625                 630                 635                 640
Leu Val Asn Gly Trp Asn Gln Lys Ala Ala Glu Leu Thr Gly Leu Arg
                645                 650                 655
Val Asp Asp Ala Ile Gly Arg His Ile Leu Thr Leu Val Glu Asp Ser
            660                 665                 670
Ser Val Pro Val Val Gln Arg Met Leu Tyr Leu Ala Leu Gln Gly Lys
        675                 680                 685
Glu Glu Lys Glu Val Arg Phe Glu Val Lys Thr His Gly Pro Lys Arg
    690                 695                 700
Asp Asp Gly Pro Val Ile Leu Val Val Asn Ala Cys Ala Ser Arg Asp
705                 710                 715                 720
Leu His Asp His Val Val Gly Val Cys Phe Val Ala Gln Asp Met Thr
                725                 730                 735
Val His Lys Leu Val Met Asp Lys Phe Thr Arg Val Glu Gly Asp Tyr
            740                 745                 750
Lys Ala Ile Ile His Asn Pro Asn Pro Leu Ile Pro Pro Ile Phe Gly
        755                 760                 765
Ala Asp Glu Phe Gly Trp Cys Ser Glu Trp Asn Ala Ala Met Thr Lys
    770                 775                 780
Leu Thr Gly Trp Asn Arg Asp Glu Val Leu Asp Lys Met Leu Leu Gly
785                 790                 795                 800
Glu Val Phe Asp Ser Ser Asn Ala Ser Cys Pro Leu Lys Asn Arg Asp
                805                 810                 815
Ala Phe Val Ser Leu Cys Val Leu Ile Asn Ser Ala Leu Ala Gly Glu
            820                 825                 830
Glu Thr Glu Lys Ala Pro Phe Gly Phe Phe Asp Arg Ser Gly Lys Tyr
        835                 840                 845
Ile Glu Cys Leu Leu Ser Ala Asn Arg Lys Glu Asn Glu Gly Gly Leu
    850                 855                 860
Ile Thr Gly Val Phe Cys Phe Ile His Val Ala Ser His Glu Leu Gln
865                 870                 875                 880
His Ala Leu Gln Val Gln Gln Ala Ser Glu Gln Thr Ser Leu Lys Arg
                885                 890                 895
Leu Lys Ala Phe Ser Tyr Met Arg His Ala Ile Asn Asn Pro Leu Ser
            900                 905                 910
Gly Met Leu Tyr Ser Arg Lys Ala Leu Lys Asn Thr Asp Leu Asn Glu
        915                 920                 925
Glu Gln Met Lys Gln Ile His Val Gly Asp Asn Cys His His Gln Ile
```

```
                930             935             940
Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
            980                 985                 990

Arg Ile Ser Cys Asn Leu Pro Glu Arg Phe Met Lys Gln Ser Val Tyr
        995                1000                1005

Gly Asp Gly Val Arg Leu Gln Gln Ile Leu Ser Asp Phe Leu Phe
   1010                1015                1020

Ile Ser Val Lys Phe Ser Pro Val Gly Gly Ser Val Glu Ile Ser
   1025                1030                1035

Ser Lys Leu Thr Lys Asn Ser Ile Gly Glu Asn Leu His Leu Ile
   1040                1045                1050

Asp Leu Glu Leu Arg Ile Lys His Gln Gly Leu Gly Val Pro Ala
   1055                1060                1065

Glu Leu Met Ala Gln Met Phe Glu Glu Asp Asn Lys Glu Gln Ser
   1070                1075                1080

Glu Glu Gly Leu Ser Leu Leu Val Ser Arg Asn Leu Leu Arg Leu
   1085                1090                1095

Met Asn Gly Asp Val Arg His Leu Arg Glu Ala Gly Val Ser Thr
   1100                1105                1110

Phe Ile Ile Thr Ala Glu Leu Ala Ser Ala Pro Thr Ala Met Gly
   1115                1120                1125

Gln

<210> SEQ ID NO 13
<211> LENGTH: 1129
<212> TYPE: PRT
<213> ORGANISM: Avena sp.

<400> SEQUENCE: 13

Met Ser Ser Ser Arg Pro Ala Ser Ser Ser Ser Arg Asn Arg Gln
1               5                  10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
        35                  40                  45

Val Glu Ala Gln Arg Asp Gly Pro Pro Val Gln Gln Gly Arg Ser Glu
    50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
            100                 105                 110

Val Pro Ser Val Asp Asp Pro Arg Leu Gly Ile Gly Thr Asn Val
        115                 120                 125

Arg Ser Leu Phe Ser Asp Gln Gly Ala Thr Ala Leu His Lys Ala Leu
    130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
```

```
                       165                 170                 175
Leu Val Val Asp Phe Glu Pro Val Lys Pro Thr Glu Phe Pro Ala Thr
                180                 185                 190
Ala Ala Gly Ala Leu Gln Ser Tyr Lys Leu Ala Ala Lys Ala Ile Ser
            195                 200                 205
Lys Ile Gln Ser Leu Pro Gly Gly Ser Met Glu Met Leu Cys Asn Thr
        210                 215                 220
Val Val Lys Glu Val Phe Asp Leu Thr Gly Tyr Asp Arg Val Met Ala
225                 230                 235                 240
Tyr Lys Phe His Glu Asp His Gly Glu Val Phe Ser Glu Ile Thr
                245                 250                 255
Lys Pro Gly Leu Glu Pro Tyr Leu Gly Leu His Tyr Pro Ala Thr Asp
                260                 265                 270
Ile Pro Gln Ala Ala Arg Phe Leu Phe Met Lys Asn Lys Val Arg Met
            275                 280                 285
Ile Cys Asp Cys Arg Ala Arg Ser Ile Lys Val Ile Glu Ala Glu Ala
        290                 295                 300
Leu Pro Trp Asp Ile Ser Leu Cys Gly Ser Ala Leu Arg Ala Pro His
305                 310                 315                 320
Ser Cys His Leu Gln Tyr Met Glu Asn Met Asn Ser Ile Ala Ser Leu
                325                 330                 335
Val Met Ala Val Val Asn Glu Asn Glu Glu Asp Asp Glu Ala Glu
                340                 345                 350
Ser Glu Gln Pro Ala Gln Gln Lys Lys Lys Leu Trp Gly Leu
        355                 360                 365
Leu Val Cys His His Glu Ser Pro Arg Tyr Val Pro Phe Pro Leu Arg
370                 375                 380
Tyr Ala Cys Glu Phe Leu Ala Gln Val Phe Ala Val His Val Asn Arg
385                 390                 395                 400
Glu Phe Glu Leu Glu Lys Gln Leu Arg Glu Lys Asn Ile Leu Lys Met
                405                 410                 415
Gln Thr Met Leu Ser Asp Met Leu Phe Arg Glu Ala Ser Pro Leu Thr
                420                 425                 430
Ile Val Ser Gly Asn Pro Asn Ile Met Asp Leu Val Lys Cys Asp Gly
            435                 440                 445
Ala Ala Leu Leu Tyr Gly Gly Lys Val Trp Arg Leu Arg Asn Ala Pro
        450                 455                 460
Thr Glu Ser Gln Ile His Asp Ile Ala Phe Trp Leu Ser Asp Val His
465                 470                 475                 480
Arg Asp Ser Thr Gly Leu Ser Thr Asp Ser Leu His Asp Ala Gly Tyr
                485                 490                 495
Pro Gly Ala Ala Ala Leu Gly Asp Met Ile Cys Gly Met Ala Val Ala
                500                 505                 510
Lys Ile Asn Ser Lys Asp Ile Leu Phe Trp Phe Arg Ser His Thr Ala
            515                 520                 525
Ala Glu Ile Arg Trp Gly Gly Ala Lys Asn Asp Pro Ser Asp Met Asp
        530                 535                 540
Asp Ser Arg Arg Met His Pro Arg Leu Ser Phe Lys Ala Phe Leu Glu
545                 550                 555                 560
Val Val Lys Met Lys Ser Leu Pro Trp Ser Asp Tyr Glu Met Asp Ala
                565                 570                 575
Ile His Ser Leu Gln Leu Ile Leu Arg Gly Thr Leu Asn Asp Ala Ser
                580                 585                 590
```

-continued

```
Lys Pro Lys Arg Glu Ala Ser Leu Asp Asn Gln Ile Gly Asp Leu Lys
            595                 600                 605

Leu Asp Gly Leu Ala Glu Leu Gln Ala Val Thr Ser Glu Met Val Arg
        610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
            660                 665                 670

Ser Val Pro Val Val Gln Arg Met Leu Tyr Leu Ala Leu Gln Gly Lys
        675                 680                 685

Glu Glu Lys Glu Val Arg Phe Glu Val Lys Thr His Gly Pro Lys Arg
    690                 695                 700

Asp Asp Gly Pro Val Ile Leu Val Val Asn Ala Cys Ala Ser Arg Asp
705                 710                 715                 720

Leu His Asp His Val Gly Val Cys Phe Val Ala Gln Asp Met Thr
                725                 730                 735

Val His Lys Leu Val Met Asp Lys Phe Thr Arg Val Glu Gly Asp Tyr
            740                 745                 750

Lys Ala Ile Ile His Asn Pro Asn Pro Leu Ile Pro Pro Ile Phe Gly
        755                 760                 765

Ala Asp Glu Phe Gly Trp Cys Ser Glu Trp Asn Ala Ala Met Thr Lys
    770                 775                 780

Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
                805                 810                 815

Ala Phe Val Ser Leu Cys Val Leu Ile Asn Ser Ala Leu Ala Gly Glu
            820                 825                 830

Glu Thr Glu Lys Ala Pro Phe Gly Phe Phe Asp Arg Ser Gly Lys Tyr
        835                 840                 845

Ile Glu Cys Leu Leu Ser Ala Asn Arg Lys Glu Asn Glu Gly Gly Leu
850                 855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
                885                 890                 895

Leu Lys Ala Phe Ser Tyr Met Arg His Ala Ile Asn Asn Pro Leu Ser
            900                 905                 910

Gly Met Leu Tyr Ser Arg Lys Ala Leu Lys Asn Thr Asp Leu Asn Glu
        915                 920                 925

Glu Gln Met Lys Gln Ile His Val Gly Asp Asn Cys His His Gln Ile
    930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
            980                 985                 990

Arg Ile Ser Cys Asn Leu Pro Glu  Arg Phe Met Lys Gln  Ser Val Tyr
        995                 1000                1005
```

```
Gly Asp Gly Val Arg Leu Gln Gln Ile Leu Ser Asp Phe Leu Phe
    1010                1015                1020

Ile Ser Val Lys Phe Ser Pro Val Gly Ser Val Glu Ile Ser
    1025                1030                1035

Ser Lys Leu Thr Lys Asn Ser Ile Gly Glu Asn Leu His Leu Ile
    1040                1045                1050

Asp Leu Glu Leu Arg Ile Lys His Gln Gly Leu Gly Val Pro Ala
    1055                1060                1065

Glu Leu Met Ala Gln Met Phe Glu Glu Asp Asn Lys Glu Gln Ser
    1070                1075                1080

Glu Glu Gly Leu Ser Leu Leu Val Ser Arg Asn Leu Leu Arg Leu
    1085                1090                1095

Met Asn Gly Asp Val Arg His Leu Arg Glu Ala Gly Val Ser Thr
    1100                1105                1110

Phe Ile Ile Thr Ala Glu Leu Ala Ser Ala Pro Thr Ala Met Gly
    1115                1120                1125

Gln

<210> SEQ ID NO 14
<211> LENGTH: 1129
<212> TYPE: PRT
<213> ORGANISM: Avena sp.

<400> SEQUENCE: 14

Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
                20                  25                  30

Asn Ala Glu Tyr Glu Glu Ser Gly Asp Ser Phe Asp Tyr Ser Lys Leu
                35                  40                  45

Val Glu Ala Gln Arg Asp Gly Pro Pro Val Gln Gln Gly Arg Ser Glu
    50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
                100                 105                 110

Val Pro Ser Val Asp Asp Pro Arg Leu Gly Ile Gly Thr Asn Val
                115                 120                 125

Arg Ser Leu Phe Ser Asp Gln Gly Ala Thr Ala Leu His Lys Ala Leu
    130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
                180                 185                 190

Ala Ala Gly Ala Leu Gln Ser Tyr Lys Leu Ala Ala Lys Ala Ile Ser
                195                 200                 205

Lys Ile Gln Ser Leu Pro Gly Gly Ser Met Glu Met Leu Cys Asn Thr
    210                 215                 220

Val Val Lys Glu Val Phe Asp Leu Thr Gly Tyr Asp Arg Val Met Ala
225                 230                 235                 240
```

-continued

```
Tyr Lys Phe His Glu Asp Asp His Gly Glu Val Phe Ser Glu Ile Thr
            245                 250                 255

Lys Pro Gly Leu Glu Pro Tyr Leu Gly Leu His Tyr Pro Ala Thr Asp
            260                 265                 270

Ile Pro Gln Ala Ala Arg Phe Leu Phe Met Lys Asn Lys Val Arg Met
            275                 280                 285

Ile Cys Asp Cys Arg Ala Arg Ser Ile Lys Val Ile Glu Ala Glu Ala
            290                 295                 300

Leu Pro Phe Asp Ile Ser Leu Cys Gly Ser Ala Leu Arg Ala Pro His
305                 310                 315                 320

Ser Cys His Leu Gln Phe Met Glu Asn Met Asn Ser Ile Ala Ser Leu
            325                 330                 335

Val Met Ala Val Val Asn Glu Asn Glu Glu Asp Glu Ala Glu
            340                 345                 350

Ser Glu Gln Pro Ala Gln Gln Lys Lys Lys Leu Trp Gly Leu
            355                 360                 365

Leu Val Cys His His Glu Ser Pro Arg Tyr Val Pro Phe Pro Leu Arg
            370                 375                 380

Tyr Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
            405                 410                 415

Gln Thr Met Leu Ser Asp Met Leu Phe Arg Glu Ala Ser Pro Leu Thr
            420                 425                 430

Ile Val Ser Gly Asn Pro Asn Ile Met Asp Leu Val Lys Cys Asp Gly
            435                 440                 445

Ala Ala Leu Leu Tyr Gly Gly Lys Val Trp Arg Leu Arg Asn Ala Pro
450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
            485                 490                 495

Pro Gly Ala Ala Ala Leu Gly Asp Met Ile Cys Gly Met Ala Val Ala
            500                 505                 510

Lys Ile Asn Ser Lys Asp Ile Leu Phe Trp Phe Arg Ser His Thr Ala
            515                 520                 525

Ala Glu Ile Arg Trp Gly Gly Ala Lys Asn Asp Pro Ser Asp Met Asp
            530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
            565                 570                 575

Ile His Ser Leu Gln Leu Ile Leu Arg Gly Thr Leu Asn Asp Ala Ser
            580                 585                 590

Lys Pro Lys Arg Glu Ala Ser Leu Asp Asn Gln Ile Gly Asp Leu Lys
            595                 600                 605

Leu Asp Gly Leu Ala Glu Leu Gln Ala Val Thr Ser Glu Met Val Arg
            610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
            645                 650                 655

Val Asp Asp Ala Ile Gly Arg His Ile Leu Thr Leu Val Glu Asp Ser
```

-continued

```
                660                 665                 670
Ser Val Pro Val Gln Arg Met Leu Tyr Leu Ala Leu Gln Gly Lys
        675                 680                 685
Glu Glu Lys Glu Val Arg Phe Glu Val Lys Thr His Gly Pro Lys Arg
690                 695                 700
Asp Asp Gly Pro Val Ile Leu Val Asn Ala Cys Ala Ser Arg Asp
705                 710                 715                 720
Leu His Asp His Val Gly Val Cys Phe Ala Gln Asp Met Thr
                725                 730                 735
Val His Lys Leu Val Met Asp Lys Phe Thr Arg Val Glu Gly Asp Tyr
            740                 745                 750
Lys Ala Ile Ile His Asn Pro Asn Pro Leu Ile Pro Pro Ile Phe Gly
            755                 760                 765
Ala Asp Glu Phe Gly Trp Cys Ser Glu Trp Asn Ala Ala Met Thr Lys
770                 775                 780
Leu Thr Gly Trp Asn Arg Asp Glu Val Leu Asp Lys Met Leu Leu Gly
785                 790                 795                 800
Glu Val Phe Asp Ser Ser Asn Ala Ser Cys Pro Leu Lys Asn Arg Asp
                805                 810                 815
Ala Phe Val Ser Leu Cys Val Leu Ile Asn Ser Ala Leu Ala Gly Glu
                820                 825                 830
Glu Thr Glu Lys Ala Pro Phe Gly Phe Phe Asp Arg Ser Gly Lys Tyr
            835                 840                 845
Ile Glu Cys Leu Leu Ser Ala Asn Arg Lys Glu Asn Glu Gly Gly Leu
            850                 855                 860
Ile Thr Gly Val Phe Cys Phe Ile His Val Ala Ser His Glu Leu Gln
865                 870                 875                 880
His Ala Leu Gln Val Gln Gln Ala Ser Glu Gln Thr Ser Leu Lys Arg
                885                 890                 895
Leu Lys Ala Phe Ser Tyr Met Arg His Ala Ile Asn Asn Pro Leu Ser
            900                 905                 910
Gly Met Leu Tyr Ser Arg Lys Ala Leu Lys Asn Thr Asp Leu Asn Glu
            915                 920                 925
Glu Gln Met Lys Gln Ile His Val Gly Asp Asn Cys His His Gln Ile
            930                 935                 940
Asn Lys Ile Leu Ala Asp Leu Asp Gln Asp Ser Ile Thr Glu Lys Ser
945                 950                 955                 960
Ser Cys Leu Asp Leu Glu Met Ala Glu Phe Leu Leu Gln Asp Val Val
                965                 970                 975
Val Ala Ala Val Ser Gln Val Leu Ile Thr Cys Gln Gly Lys Gly Ile
                980                 985                 990
Arg Ile Ser Cys Asn Leu Pro Glu  Arg Phe Met Lys Gln  Ser Val Tyr
            995                 1000                1005
Gly Asp  Gly Val Arg Leu Gln  Gln Ile Leu Ser Asp  Phe Leu Phe
        1010                1015                1020
Ile Ser  Val Lys Phe Ser Pro  Val Gly Gly Ser Val  Glu Ile Ser
        1025                1030                1035
Ser Lys  Leu Thr Lys Asn Ser  Ile Gly Glu Asn Leu  His Leu Ile
        1040                1045                1050
Asp Leu  Glu Leu Arg Ile Lys  His Gln Gly Leu Gly  Val Pro Ala
        1055                1060                1065
Glu Leu  Met Ala Gln Met Phe  Glu Glu Asp Asn Lys  Glu Gln Ser
        1070                1075                1080
```

```
Glu Glu Gly Leu Ser Leu Leu Val Ser Arg Asn Leu Leu Arg Leu
    1085                1090                1095

Met Asn Gly Asp Val Arg His Leu Arg Glu Ala Gly Val Ser Thr
    1100                1105                1110

Phe Ile Ile Thr Ala Glu Leu Ala Ser Ala Pro Thr Ala Met Gly
    1115                1120                1125

Gln

<210> SEQ ID NO 15
<211> LENGTH: 1129
<212> TYPE: PRT
<213> ORGANISM: Avena sp.

<400> SEQUENCE: 15

Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
            35                  40                  45

Val Glu Ala Gln Arg Asp Gly Pro Pro Val Gln Gln Gly Arg Ser Glu
50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
            100                 105                 110

Val Pro Ser Val Asp Asp Pro Arg Leu Gly Ile Gly Thr Asn Val
            115                 120                 125

Arg Ser Leu Phe Ser Asp Gln Gly Ala Thr Ala Leu His Lys Ala Leu
    130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
            180                 185                 190

Ala Ala Gly Ala Leu Gln Ser Tyr Lys Leu Ala Ala Lys Ala Ile Ser
            195                 200                 205

Lys Ile Gln Ser Leu Pro Gly Gly Ser Met Glu Met Leu Cys Asn Thr
    210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
            260                 265                 270

Ile Pro Gln Ala Ala Arg Phe Leu Phe Met Lys Asn Lys Val Arg Met
            275                 280                 285

Ile Cys Asp Cys Arg Ala Arg Ser Ile Lys Val Ile Glu Ala Glu Ala
    290                 295                 300

Leu Pro Phe Asp Ile Val Leu Cys Gly Ser Ala Leu Arg Ala Pro His
305                 310                 315                 320
```

-continued

```
Ser Cys His Leu Gln Tyr Met Glu Asn Met Asn Ser Ile Ala Ser Leu
                325                 330                 335

Val Met Ala Val Val Asn Glu Asn Glu Glu Asp Asp Glu Ala Glu
            340                 345                 350

Ser Glu Gln Pro Ala Gln Gln Lys Lys Lys Leu Trp Gly Leu
            355                 360                 365

Leu Val Cys His His Glu Ser Pro Arg Tyr Val Pro Phe Pro Leu Arg
    370                 375                 380

Tyr Ala Cys Glu Phe Leu Ala Gln Val Phe Ala Val His Val Asn Arg
385                 390                 395                 400

Glu Phe Glu Leu Glu Lys Gln Leu Arg Glu Lys Asn Ile Leu Lys Met
                405                 410                 415

Gln Thr Met Leu Ser Asp Met Leu Phe Arg Glu Ala Ser Pro Leu Thr
                420                 425                 430

Ile Val Ser Gly Asn Pro Asn Ile Met Asp Leu Val Lys Cys Asp Gly
            435                 440                 445

Ala Ala Leu Leu Tyr Gly Gly Lys Val Trp Arg Leu Arg Asn Ala Pro
    450                 455                 460

Thr Glu Ser Gln Ile His Asp Ile Ala Phe Trp Leu Ser Asp Val His
465                 470                 475                 480

Arg Asp Ser Thr Gly Leu Ser Thr Asp Ser Leu His Asp Ala Gly Tyr
                485                 490                 495

Pro Gly Ala Ala Ala Leu Gly Asp Met Ile Cys Gly Met Ala Val Ala
            500                 505                 510

Lys Ile Asn Ser Lys Asp Ile Leu Phe Trp Phe Arg Ser His Thr Ala
    515                 520                 525

Ala Glu Ile Arg Trp Gly Gly Ala Lys Asn Asp Pro Ser Asp Met Asp
            530                 535                 540

Asp Ser Arg Arg Met His Pro Arg Leu Ser Phe Lys Ala Phe Leu Glu
545                 550                 555                 560

Val Val Lys Met Lys Ser Leu Pro Trp Ser Asp Tyr Glu Met Asp Ala
                565                 570                 575

Ile His Ser Leu Gln Leu Ile Leu Arg Gly Thr Leu Asn Asp Ala Ser
                580                 585                 590

Lys Pro Lys Arg Glu Ala Ser Leu Asp Asn Gln Ile Gly Asp Leu Lys
            595                 600                 605

Leu Asp Gly Leu Ala Glu Leu Gln Ala Val Thr Ser Glu Met Val Arg
    610                 615                 620

Leu Met Glu Thr Ala Thr Val Pro Ile Leu Ala Val Asp Gly Asn Gly
625                 630                 635                 640

Leu Val Asn Gly Trp Asn Gln Lys Ala Ala Glu Leu Thr Gly Leu Arg
                645                 650                 655

Val Asp Asp Ala Ile Gly Arg His Ile Leu Thr Leu Val Glu Asp Ser
            660                 665                 670

Ser Val Pro Val Val Gln Arg Met Leu Tyr Leu Ala Leu Gln Gly Lys
    675                 680                 685

Glu Glu Lys Glu Val Arg Phe Glu Val Lys Thr His Gly Pro Lys Arg
            690                 695                 700

Asp Asp Gly Pro Val Ile Leu Val Val Asn Ala Cys Ala Ser Arg Asp
705                 710                 715                 720

Leu His Asp His Val Val Gly Val Cys Phe Val Ala Gln Asp Met Thr
                725                 730                 735
```

```
Val His Lys Leu Val Met Asp Lys Phe Thr Arg Val Glu Gly Asp Tyr
            740                 745                 750

Lys Ala Ile Ile His Asn Pro Asn Pro Leu Ile Pro Pro Ile Phe Gly
        755                 760                 765

Ala Asp Glu Phe Gly Trp Cys Ser Glu Trp Asn Ala Ala Met Thr Lys
    770                 775                 780

Leu Thr Gly Trp Asn Arg Asp Glu Val Leu Asp Lys Met Leu Leu Gly
785                 790                 795                 800

Glu Val Phe Asp Ser Ser Asn Ala Ser Cys Pro Leu Lys Asn Arg Asp
                805                 810                 815

Ala Phe Val Ser Leu Cys Val Leu Ile Asn Ser Ala Leu Ala Gly Glu
                820                 825                 830

Glu Thr Glu Lys Ala Pro Phe Gly Phe Phe Asp Arg Ser Gly Lys Tyr
            835                 840                 845

Ile Glu Cys Leu Leu Ser Ala Asn Arg Lys Glu Asn Glu Gly Gly Leu
    850                 855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
                885                 890                 895

Leu Lys Ala Phe Ser Tyr Met Arg His Ala Ile Asn Asn Pro Leu Ser
            900                 905                 910

Gly Met Leu Tyr Ser Arg Lys Ala Leu Lys Asn Thr Asp Leu Asn Glu
        915                 920                 925

Glu Gln Met Lys Gln Ile His Val Gly Asp Asn Cys His His Gln Ile
    930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
                980                 985                 990

Arg Ile Ser Cys Asn Leu Pro Glu Arg Phe Met Lys Gln Ser Val Tyr
            995                1000                1005

Gly Asp Gly Val Arg Leu Gln Gln Ile Leu Ser Asp Phe Leu Phe
        1010                1015                1020

Ile Ser Val Lys Phe Ser Pro Val Gly Gly Ser Val Glu Ile Ser
    1025                1030                1035

Ser Lys Leu Thr Lys Asn Ser Ile Gly Glu Asn Leu His Leu Ile
    1040                1045                1050

Asp Leu Glu Leu Arg Ile Lys His Gln Gly Leu Gly Val Pro Ala
    1055                1060                1065

Glu Leu Met Ala Gln Met Phe Glu Glu Asp Asn Lys Glu Gln Ser
    1070                1075                1080

Glu Glu Gly Leu Ser Leu Val Ser Arg Asn Leu Leu Arg Leu
    1085                1090                1095

Met Asn Gly Asp Val Arg His Leu Arg Glu Ala Gly Val Ser Thr
    1100                1105                1110

Phe Ile Ile Thr Ala Glu Leu Ala Ser Ala Pro Thr Ala Met Gly
    1115                1120                1125

Gln
```

<210> SEQ ID NO 16

```
<211> LENGTH: 1129
<212> TYPE: PRT
<213> ORGANISM: Avena sp.

<400> SEQUENCE: 16

Met Ser Ser Ser Arg Pro Ala Ser Ser Ser Ser Arg Asn Arg Gln
1               5                   10                  15

Ser Ser Gln Ala Arg Val Leu Ala Gln Thr Thr Leu Asp Ala Glu Leu
            20                  25                  30

Asn Ala Glu Tyr Glu Glu Ser Gly Asp Ser Phe Asp Tyr Ser Lys Leu
        35                  40                  45

Val Glu Ala Gln Arg Asp Gly Pro Pro Val Gln Gln Gly Arg Ser Glu
    50                  55                  60

Lys Val Ile Ala Tyr Leu Gln His Ile Gln Lys Gly Lys Leu Ile Gln
65                  70                  75                  80

Thr Phe Gly Cys Leu Leu Ala Leu Asp Glu Lys Ser Phe Asn Val Ile
                85                  90                  95

Ala Phe Ser Glu Asn Ala Pro Glu Met Leu Thr Thr Val Ser His Ala
            100                 105                 110

Val Pro Ser Val Asp Asp Pro Arg Leu Gly Ile Gly Thr Asn Val
        115                 120                 125

Arg Ser Leu Phe Ser Asp Gln Gly Ala Thr Ala Leu His Lys Ala Leu
    130                 135                 140

Gly Phe Ala Asp Val Ser Leu Leu Asn Pro Ile Leu Val Gln Cys Lys
145                 150                 155                 160

Thr Ser Gly Lys Pro Phe Tyr Ala Ile Val His Arg Ala Thr Gly Cys
                165                 170                 175

Leu Val Val Asp Phe Glu Pro Val Lys Pro Thr Glu Phe Pro Ala Thr
            180                 185                 190

Ala Ala Gly Ala Leu Gln Ser Tyr Lys Leu Ala Ala Lys Ala Ile Ser
        195                 200                 205

Lys Ile Gln Ser Leu Pro Gly Gly Ser Met Glu Met Leu Cys Asn Thr
    210                 215                 220

Val Val Lys Glu Val Phe Asp Leu Thr Gly Tyr Asp Arg Val Met Ala
225                 230                 235                 240

Tyr Lys Phe His Glu Asp Asp His Gly Glu Val Phe Ser Glu Ile Thr
                245                 250                 255

Lys Pro Gly Leu Glu Pro Tyr Leu Gly Leu His Tyr Pro Ala Thr Asp
            260                 265                 270

Ile Pro Gln Ala Ala Arg Phe Leu Phe Met Lys Asn Lys Val Arg Met
        275                 280                 285

Ile Cys Asp Cys Arg Ala Arg Ser Ile Lys Val Ile Glu Ala Glu Ala
    290                 295                 300

Leu Pro Phe Asp Ile Ser Leu Cys Gly Ser Ala Leu Glu Ala Pro His
305                 310                 315                 320

Ser Cys His Leu Gln Tyr Met Glu Asn Met Asn Ser Ile Ala Ser Leu
                325                 330                 335

Val Met Ala Val Val Asn Glu Asn Glu Glu Asp Asp Glu Ala Glu
            340                 345                 350

Ser Glu Gln Pro Ala Gln Gln Lys Lys Lys Leu Trp Gly Leu
        355                 360                 365

Leu Val Cys His His Glu Ser Pro Arg Tyr Val Pro Phe Pro Leu Arg
    370                 375                 380

Tyr Ala Cys Glu Phe Leu Ala Gln Val Phe Ala Val His Val Asn Arg
```

-continued

```
            385                 390                 395                 400
    Glu Phe Glu Leu Glu Lys Gln Leu Arg Glu Lys Asn Ile Leu Lys Met
                    405                 410                 415

Gln Thr Met Leu Ser Asp Met Leu Phe Arg Glu Ala Ser Pro Leu Thr
                    420                 425                 430

Ile Val Ser Gly Asn Pro Asn Ile Met Asp Leu Val Lys Cys Asp Gly
                    435                 440                 445

Ala Ala Leu Leu Tyr Gly Gly Lys Val Trp Arg Leu Arg Asn Ala Pro
                    450                 455                 460

Thr Glu Ser Gln Ile His Asp Ile Ala Phe Trp Leu Ser Asp Val His
    465                 470                 475                 480

Arg Asp Ser Thr Gly Leu Ser Thr Asp Ser Leu His Asp Ala Gly Tyr
                    485                 490                 495

Pro Gly Ala Ala Ala Leu Gly Asp Met Ile Cys Gly Met Ala Val Ala
                    500                 505                 510

Lys Ile Asn Ser Lys Asp Ile Leu Phe Trp Phe Arg Ser His Thr Ala
                    515                 520                 525

Ala Glu Ile Arg Trp Gly Gly Ala Lys Asn Asp Pro Ser Asp Met Asp
                    530                 535                 540

Asp Ser Arg Arg Met His Pro Arg Leu Ser Phe Lys Ala Phe Leu Glu
    545                 550                 555                 560

Val Val Lys Met Lys Ser Leu Pro Trp Ser Asp Tyr Glu Met Asp Ala
                    565                 570                 575

Ile His Ser Leu Gln Leu Ile Leu Arg Gly Thr Leu Asn Asp Ala Ser
                    580                 585                 590

Lys Pro Lys Arg Glu Ala Ser Leu Asp Asn Gln Ile Gly Asp Leu Lys
                    595                 600                 605

Leu Asp Gly Leu Ala Glu Leu Gln Ala Val Thr Ser Glu Met Val Arg
                    610                 615                 620

Leu Met Glu Thr Ala Thr Val Pro Ile Leu Ala Val Asp Gly Asn Gly
    625                 630                 635                 640

Leu Val Asn Gly Trp Asn Gln Lys Ala Ala Glu Leu Thr Gly Leu Arg
                    645                 650                 655

Val Asp Asp Ala Ile Gly Arg His Ile Leu Thr Leu Val Glu Asp Ser
                    660                 665                 670

Ser Val Pro Val Val Gln Arg Met Leu Tyr Leu Ala Leu Gln Gly Lys
                    675                 680                 685

Glu Glu Lys Glu Val Arg Phe Glu Val Lys Thr His Gly Pro Lys Arg
                    690                 695                 700

Asp Asp Gly Pro Val Ile Leu Val Val Asn Ala Cys Ala Ser Arg Asp
    705                 710                 715                 720

Leu His Asp His Val Gly Val Cys Phe Val Ala Gln Asp Met Thr
                    725                 730                 735

Val His Lys Leu Val Met Asp Lys Phe Thr Arg Val Glu Gly Asp Tyr
                    740                 745                 750

Lys Ala Ile Ile His Asn Pro Asn Pro Leu Ile Pro Pro Ile Phe Gly
                    755                 760                 765

Ala Asp Glu Phe Gly Trp Cys Ser Glu Trp Asn Ala Ala Met Thr Lys
                    770                 775                 780

Leu Thr Gly Trp Asn Arg Asp Glu Val Leu Asp Lys Met Leu Leu Gly
    785                 790                 795                 800

Glu Val Phe Asp Ser Ser Asn Ala Ser Cys Pro Leu Lys Asn Arg Asp
                    805                 810                 815
```

```
Ala Phe Val Ser Leu Cys Val Leu Ile Asn Ser Ala Leu Ala Gly Glu
            820                 825                 830

Glu Thr Glu Lys Ala Pro Phe Gly Phe Phe Asp Arg Ser Gly Lys Tyr
            835                 840                 845

Ile Glu Cys Leu Leu Ser Ala Asn Arg Lys Glu Asn Glu Gly Gly Leu
            850                 855                 860

Ile Thr Gly Val Phe Cys Phe Ile His Val Ala Ser His Glu Leu Gln
865                 870                 875                 880

His Ala Leu Gln Val Gln Gln Ala Ser Glu Gln Thr Ser Leu Lys Arg
                885                 890                 895

Leu Lys Ala Phe Ser Tyr Met Arg His Ala Ile Asn Asn Pro Leu Ser
            900                 905                 910

Gly Met Leu Tyr Ser Arg Lys Ala Leu Lys Asn Thr Asp Leu Asn Glu
            915                 920                 925

Glu Gln Met Lys Gln Ile His Val Gly Asp Asn Cys His His Gln Ile
            930                 935                 940

Asn Lys Ile Leu Ala Asp Leu Asp Gln Asp Ser Ile Thr Glu Lys Ser
945                 950                 955                 960

Ser Cys Leu Asp Leu Glu Met Ala Glu Phe Leu Leu Gln Asp Val Val
                965                 970                 975

Val Ala Ala Val Ser Gln Val Leu Ile Thr Cys Gln Gly Lys Gly Ile
            980                 985                 990

Arg Ile Ser Cys Asn Leu Pro Glu  Arg Phe Met Lys Gln  Ser Val Tyr
            995                 1000                1005

Gly Asp  Gly Val Arg Leu Gln  Gln Ile Leu Ser Asp  Phe Leu Phe
    1010                1015                1020

Ile Ser  Val Lys Phe Ser Pro  Val Gly Gly Ser Val  Glu Ile Ser
    1025                1030                1035

Ser Lys  Leu Thr Lys Asn Ser  Ile Gly Glu Asn Leu  His Leu Ile
    1040                1045                1050

Asp Leu  Glu Leu Arg Ile Lys  His Gln Gly Leu Gly  Val Pro Ala
    1055                1060                1065

Glu Leu  Met Ala Gln Met Phe  Glu Glu Asp Asn Lys  Glu Gln Ser
    1070                1075                1080

Glu Glu  Gly Leu Ser Leu Leu  Val Ser Arg Asn Leu  Leu Arg Leu
    1085                1090                1095

Met Asn  Gly Asp Val Arg His  Leu Arg Glu Ala Gly  Val Ser Thr
    1100                1105                1110

Phe Ile  Ile Thr Ala Glu Leu  Ala Ser Ala Pro Thr  Ala Met Gly
    1115                1120                1125

Gln

<210> SEQ ID NO 17
<211> LENGTH: 35
<212> TYPE: DNA
<213> ORGANISM: Primer

<400> SEQUENCE: 17
cgggatccac catggcttcc tcaaggcctg cttcc                              35

<210> SEQ ID NO 18
<211> LENGTH: 30
<212> TYPE: DNA
<213> ORGANISM: Primer
```

-continued

```
<400> SEQUENCE: 18
cgcccgggct gcagagctag atatagcatc                                    30

<210> SEQ ID NO 19
<211> LENGTH: 31
<212> TYPE: DNA
<213> ORGANISM: Primer

<400> SEQUENCE: 19
tcgcgtcgac ttgtcccatt gctgttggag c                                  31

<210> SEQ ID NO 20
<211> LENGTH: 32
<212> TYPE: DNA
<213> ORGANISM: Primer

<400> SEQUENCE: 20
ggtcttgagc cttttcttgg actgcactat cc                                 32

<210> SEQ ID NO 21
<211> LENGTH: 28
<212> TYPE: DNA
<213> ORGANISM: Primer

<400> SEQUENCE: 21
gattgccgtg cgcgcgccat aaaaggtc                                      28

<210> SEQ ID NO 22
<211> LENGTH: 29
<212> TYPE: DNA
<213> ORGANISM: Primer

<400> SEQUENCE: 22
gaggcactcc cgcgggatat tagcctatg                                     29

<210> SEQ ID NO 23
<211> LENGTH: 35
<212> TYPE: DNA
<213> ORGANISM: Primer

<400> SEQUENCE: 23
gctgaggcac tcccatggga tattagccta tgtgg                              35

<210> SEQ ID NO 24
<211> LENGTH: 28
<212> TYPE: DNA
<213> ORGANISM: Primer

<400> SEQUENCE: 24
gcactcccct ttaaaatttg cctatgtg                                      28

<210> SEQ ID NO 25
<211> LENGTH: 31
<212> TYPE: DNA
<213> ORGANISM: Primer

<400> SEQUENCE: 25
ctcccctttg atatcgtcct atgtggttca g                                  31

<210> SEQ ID NO 26
<211> LENGTH: 27
<212> TYPE: DNA
<213> ORGANISM: Primer
```

```
<400> SEQUENCE: 26
gcctatgtgg gctagcactc agggcac                                    27

<210> SEQ ID NO 27
<211> LENGTH: 26
<212> TYPE: DNA
<213> ORGANISM: Primer

<400> SEQUENCE: 27
ggttcagcac tcgaggcacc acacag                                     26

<210> SEQ ID NO 28
<211> LENGTH: 31
<212> TYPE: DNA
<213> ORGANISM: Primer

<400> SEQUENCE: 28
cagttgtcac ctgcagttta tggagaacat g                               31

<210> SEQ ID NO 29
<211> LENGTH: 23
<212> TYPE: DNA
<213> ORGANISM: Primer

<400> SEQUENCE: 29
gaagaaacta ttcggcctcc ttg                                        23

<210> SEQ ID NO 30
<211> LENGTH: 27
<212> TYPE: DNA
<213> ORGANISM: Primer

<400> SEQUENCE: 30
ggcctccttg ttgcgcacca tgagagc                                    27

<210> SEQ ID NO 31
<211> LENGTH: 33
<212> TYPE: DNA
<213> ORGANISM: Primer

<400> SEQUENCE: 31
ccgctgcgtg ctgcatgcga gttcttagca cag                             33

<210> SEQ ID NO 32
<211> LENGTH: 31
<212> TYPE: DNA
<213> ORGANISM: Primer

<400> SEQUENCE: 32
ccgctgcgtt ttgcatgcga gttcttagca c                               31

<210> SEQ ID NO 33
<211> LENGTH: 34
<212> TYPE: DNA
<213> ORGANISM: Primer

<400> SEQUENCE: 33
ccgctgcgtg ttggcatgcg agttcttagc acag                            34

<210> SEQ ID NO 34
<211> LENGTH: 33
<212> TYPE: DNA
```

```
<213> ORGANISM: Primer

<400> SEQUENCE: 34
ccgctgcgtt gggcatgcga gttcttagca cag                                    33

<210> SEQ ID NO 35
<211> LENGTH: 29
<212> TYPE: DNA
<213> ORGANISM: Primer

<400> SEQUENCE: 35
gttatgcttg tgaggcctta gcacaggtg                                         29

<210> SEQ ID NO 36
<211> LENGTH: 27
<212> TYPE: DNA
<213> ORGANISM: Primer

<400> SEQUENCE: 36
gttatgcttg tgagtactta gcacagg                                           27

<210> SEQ ID NO 37
<211> LENGTH: 29
<212> TYPE: DNA
<213> ORGANISM: Primer

<400> SEQUENCE: 37
gaggcactcc cgcgggatat tagcctatg                                         29

<210> SEQ ID NO 38
<211> LENGTH: 27
<212> TYPE: DNA
<213> ORGANISM: Primer

<400> SEQUENCE: 38
ggcctccttg ttgcgcacca tgagagc                                           27
```